United States Patent

Lund

Patent Number: 5,864,229
Date of Patent: Jan. 26, 1999

[54] EDDY CURRENT PROBE SYSTEM AND METHOD FOR DETERMINING THE MIDPOINT AND DEPTH OF A DISCONTINUITY

[75] Inventor: Frank Philip Lund, Shirrell Heath, United Kingdom

[73] Assignee: Millstrong Limited, Hants, United Kingdom

[21] Appl. No.: 897,120

[22] Filed: Jun. 11, 1992

[30] Foreign Application Priority Data

Jun. 11, 1991 [GB] United Kingdom ............... 9112546
Aug. 9, 1991 [GB] United Kingdom ............... 9117307
Aug. 30, 1991 [GB] United Kingdom ............... 9118715
Dec. 20, 1991 [GB] United Kingdom ............... 9127109

[51] Int. Cl.$^6$ .................... G01R 33/12; G01N 27/82; G01N 27/72
[52] U.S. Cl. .................... 324/240; 324/242; 324/260
[58] Field of Search .................... 324/239, 243, 324/262, 236–238, 219–221

[56] References Cited

U.S. PATENT DOCUMENTS 2,532,929 12/1950 McBrayer .
2,611,006 9/1952 Delmhorst .

(List continued on next page.)

FOREIGN PATENT DOCUMENTS

| 0 019 091 | 11/1980 | European Pat. Off. . |
| 0 081 244 | 6/1983 | European Pat. Off. . |
| 0 107 844 | 5/1984 | European Pat. Off. . |
| 0 228 177 | 11/1985 | European Pat. Off. . |
| 0 165 051 | 12/1985 | European Pat. Off. . |
| 0 1656 761 | 12/1985 | European Pat. Off. . |
| 0 171 118 | 2/1986 | European Pat. Off. . |
| 0 181 512 | 5/1986 | European Pat. Off. . |
| 0 219 477 | 4/1987 | European Pat. Off. . |
| 0 258 548 | 3/1988 | European Pat. Off. . |
| 0 260 355 | 3/1988 | European Pat. Off. . |
| 0 368 580 | 7/1988 | European Pat. Off. . |
| 0 279 258 | 8/1988 | European Pat. Off. . |
| 0 321 013 | 6/1989 | European Pat. Off. . |
| 0 381 848 | 8/1990 | European Pat. Off. . |
| 268597 | 4/1927 | United Kingdom . |
| 426238 | 3/1935 | United Kingdom . |
| 789102 | 1/1958 | United Kingdom . |
| 804323 | 11/1958 | United Kingdom . |
| 917409 | 2/1963 | United Kingdom . |
| 922225 | 3/1963 | United Kingdom . |
| 955157 | 4/1964 | United Kingdom . |
| 1101011 | 1/1968 | United Kingdom . |
| 1365129 | 8/1974 | United Kingdom . |
| 2 012 965 | 1/1979 | United Kingdom . |
| 2 082 330 | 3/1982 | United Kingdom . |
| 2 109 113 | 5/1983 | United Kingdom . |
| 2 113 405 | 8/1983 | United Kingdom . |
| 2 186 372 | 8/1987 | United Kingdom . |
| 2 192 993 | 1/1988 | United Kingdom . |
| 2 201 789 | 9/1988 | United Kingdom . |
| 2 211 617 | 7/1989 | United Kingdom . |
| 2 224 575 | 5/1990 | United Kingdom . |
| 2 225 115 | 5/1990 | United Kingdom . |
| 2 225 117 | 5/1990 | United Kingdom . |
| 2 233 763 | 1/1991 | United Kingdom . |
| WO 86/01602 | 3/1986 | WIPO . |

OTHER PUBLICATIONS

Nyenhuis et al., IEEE Transactions on Magnetics, Mag–23(5):3789–3791, Sep. 1987.
Kampfner et al., Flexible Body–Current Coil Arrays, Electric Power Research Institute, Sep. 1986, California (pp. 5–51 to 5–69).

*Primary Examiner*—Walter E. Snow
*Attorney, Agent, or Firm*—Sterne, Kessler, Goldstein & Fox P.L.L.C.

[57] ABSTRACT

A probe for generating a signal indicative of a quantitative measurement of the size of a surface defect, comprising a magnetic field generator for inducing currents in the surface, and a perturbation current sensor arrangement positioned relative to the field to give an output providing the quantitative measure.

27 Claims, 30 Drawing Sheets

U.S. PATENT DOCUMENTS

| | | | |
|---|---|---|---|
| 2,889,514 | 6/1959 | Cowan et al. . | |
| 2,958,818 | 11/1960 | Cowan et al. . | |
| 3,267,418 | 8/1966 | Wolfe . | |
| 3,303,418 | 2/1967 | Rose . | |
| 3,412,325 | 11/1968 | Soderling . | |
| 3,504,276 | 3/1970 | Proctor et al. . | |
| 3,504,664 | 4/1970 | Haddad . | |
| 3,523,241 | 8/1970 | Barton . | |
| 3,579,099 | 5/1971 | Kanabayashi | 324/235 |
| 3,609,531 | 9/1971 | Förster | 324/232 X |
| 3,670,239 | 6/1972 | Shiraiwa et al. | 324/235 |
| 3,864,627 | 2/1975 | Shigo . | |
| 3,875,502 | 4/1975 | Neumaier . | |
| 3,916,304 | 10/1975 | Roemer et al. . | |
| 3,927,370 | 12/1975 | De Bough . | |
| 4,048,558 | 9/1977 | Goodman . | |
| 4,247,819 | 1/1981 | Shimada et al. | 324/233 |
| 4,266,185 | 5/1981 | Charlesworth et al. . | |
| 4,271,393 | 6/1981 | Hansen et al. | 324/240 |
| 4,325,026 | 4/1982 | Cooper et al. . | |
| 4,388,593 | 6/1983 | Mittleman . | |
| 4,481,471 | 11/1984 | Miller et al. | 324/240 |
| 4,543,528 | 9/1985 | Baraona | 324/262 |
| 4,651,093 | 3/1987 | Detriche et al. | 324/232 |
| 4,683,419 | 7/1987 | Neuelmann et al. . | |
| 4,742,298 | 5/1988 | Ando et al. | 324/220 |
| 4,763,070 | 8/1988 | Hüchelrath | 324/225 |
| 4,839,593 | 6/1989 | Spies | 324/240 |
| 4,843,319 | 6/1989 | Lara | 324/240 |
| 4,843,320 | 6/1989 | Spies | 324/240 |
| 4,864,233 | 9/1989 | Harrison | 324/240 X |
| 4,924,181 | 5/1990 | Hüchelrath | 324/235 |
| 5,004,724 | 4/1991 | De | 324/240 X |
| 5,019,777 | 5/1991 | Gulliver et al. . | |
| 5,047,719 | 9/1991 | Johnson et al. | 324/242 |
| 5,068,608 | 11/1991 | Clark, Jr. | 324/220 |
| 5,119,023 | 6/1992 | Lloyd | 324/220 |
| 5,130,652 | 7/1992 | Kawakami et al. | 324/240 |
| 5,237,271 | 8/1993 | Hedengren | 324/240 X |

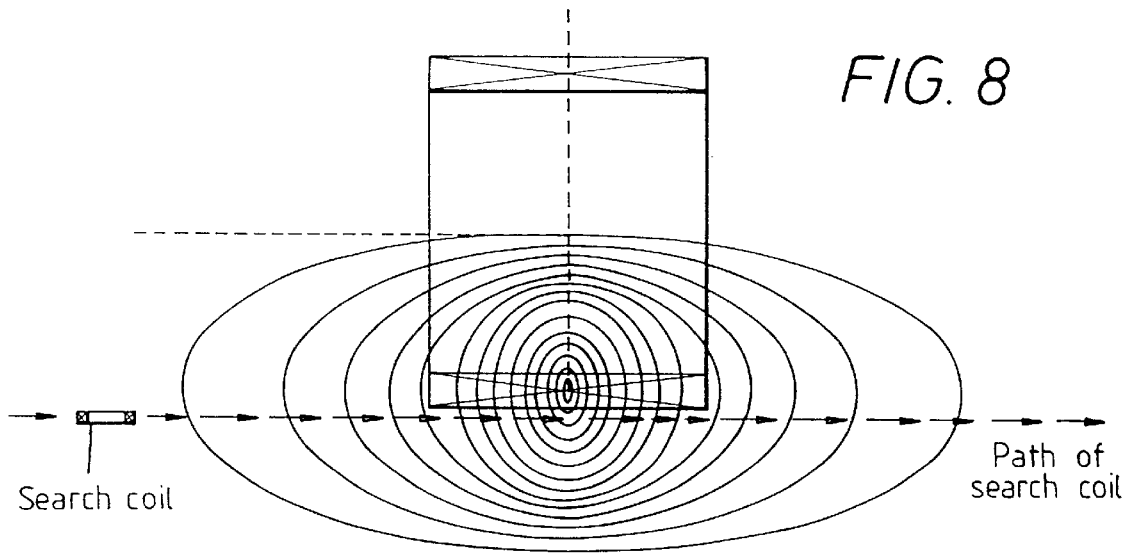
FIG. 8
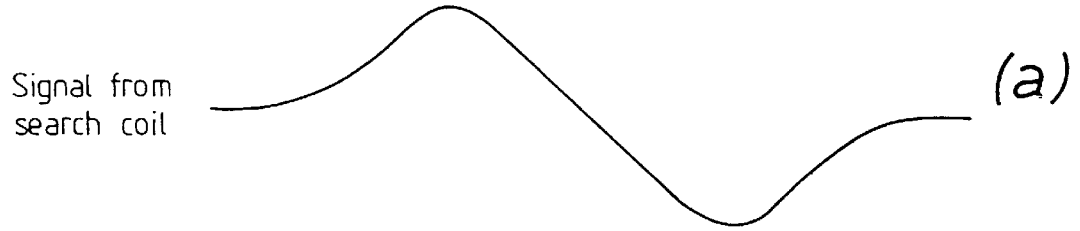
Signal from search coil
(a)
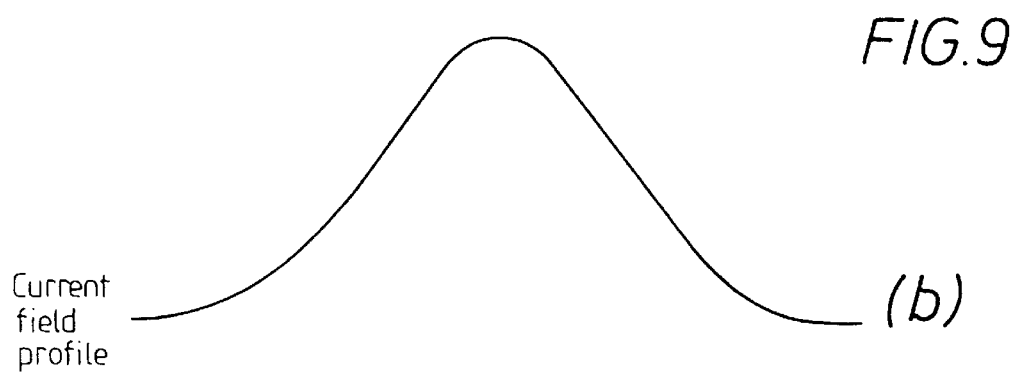
Current field profile
(b)
FIG. 9

Voltage across defect for various depths D
— Increasing depth D
— Reducing depth D Voltage gradient along the defect for various depths of defect
— Increasing depth D
— Reducing depth D

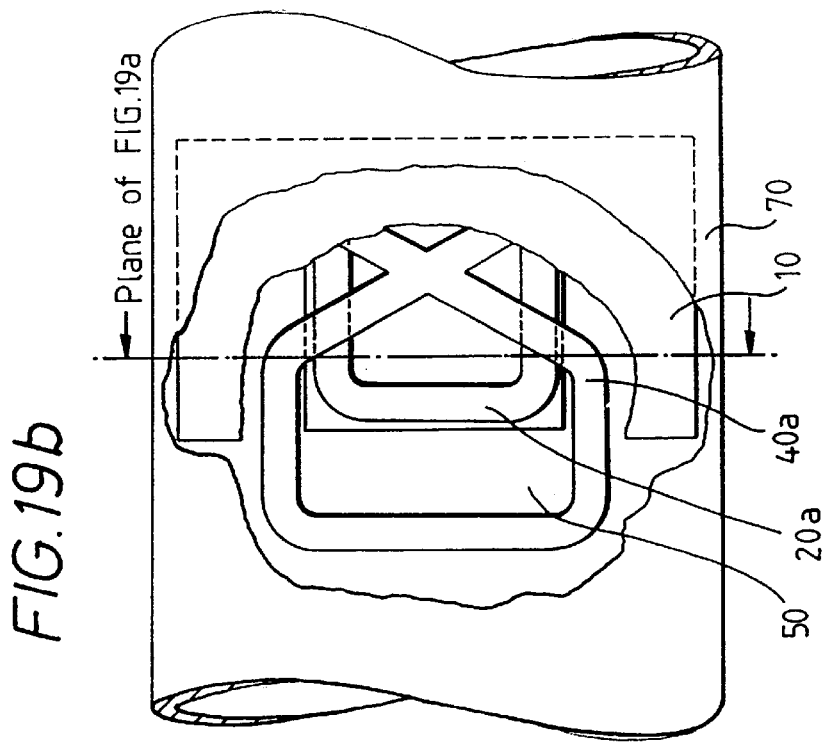
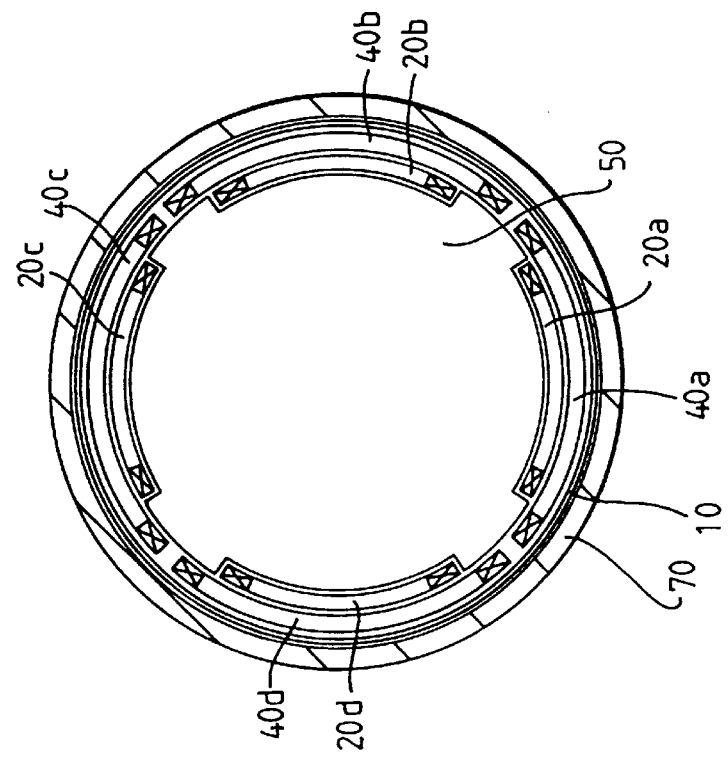

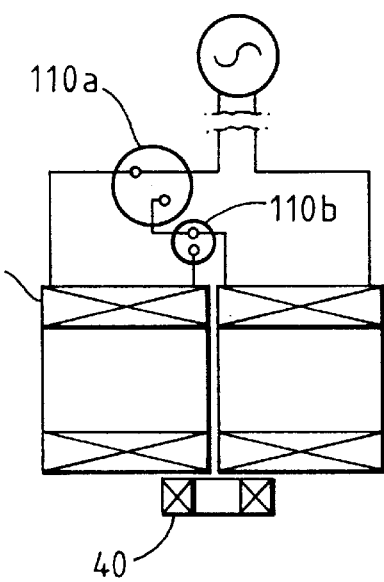
FIG. 22a
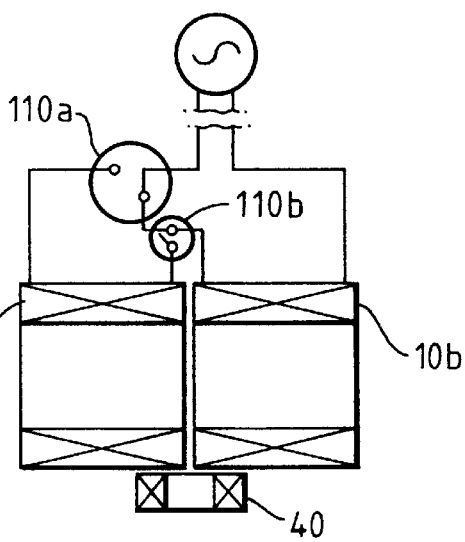
FIG. 22b
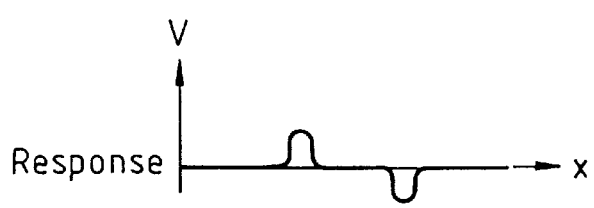
FIG. 23a
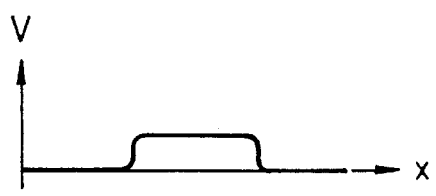
FIG. 23b
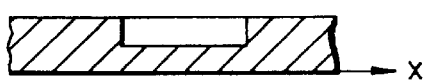

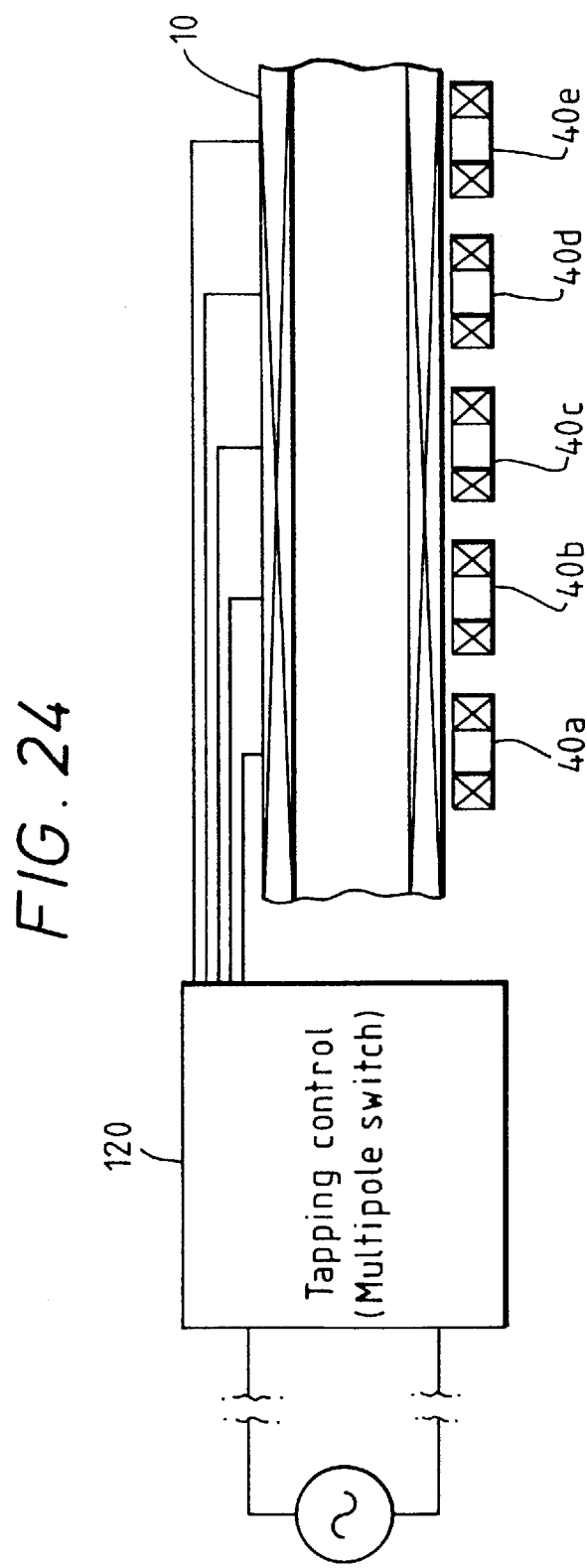

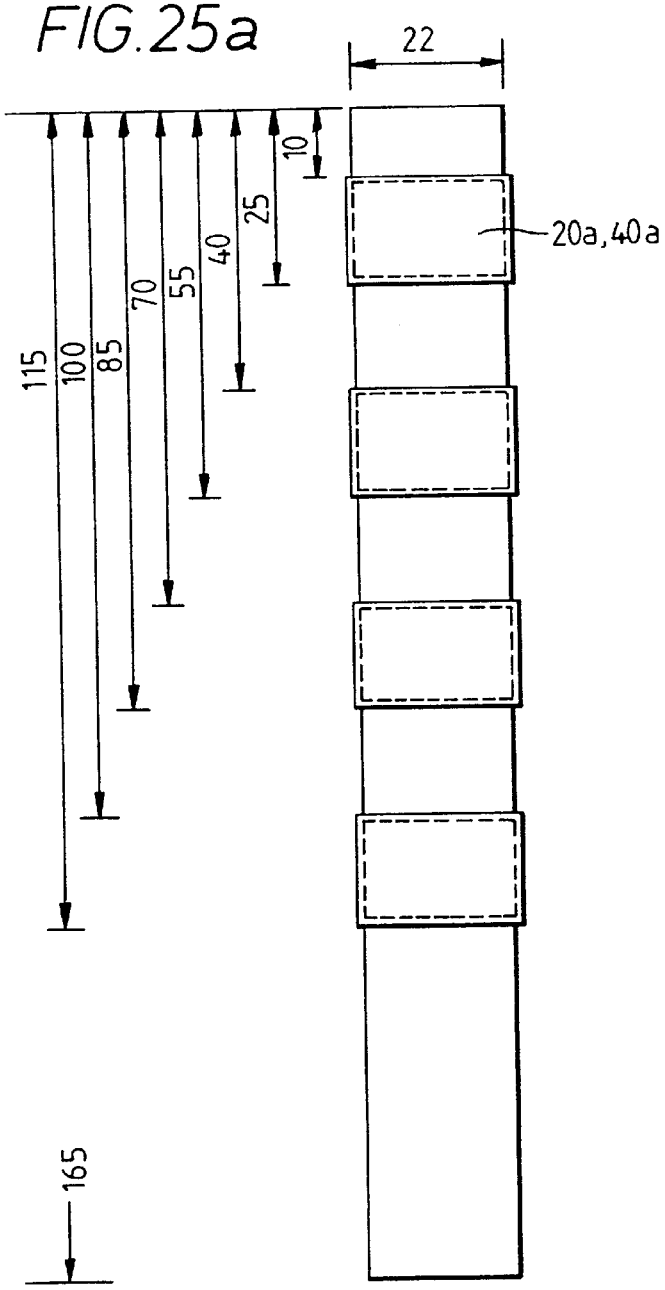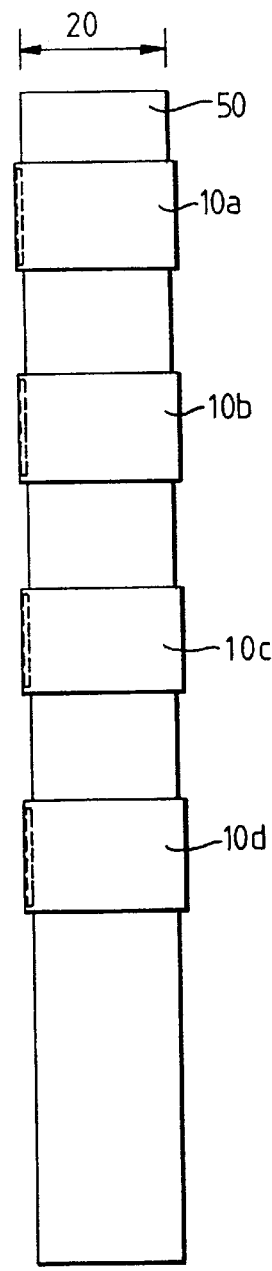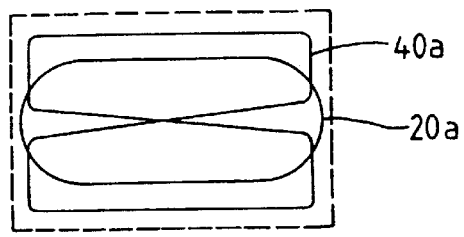

FIG. 30a
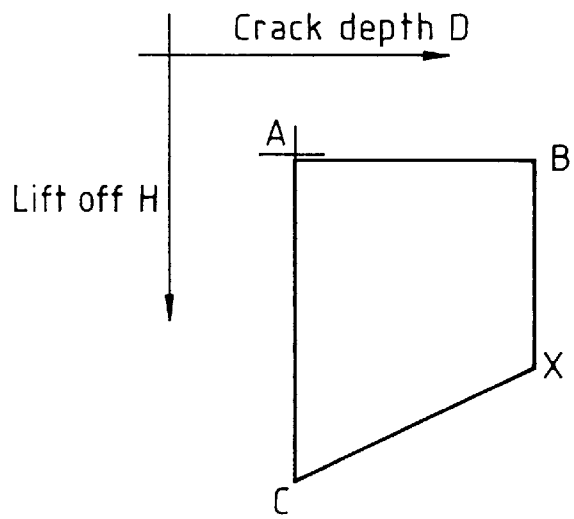
FIG. 30b (Prior art)
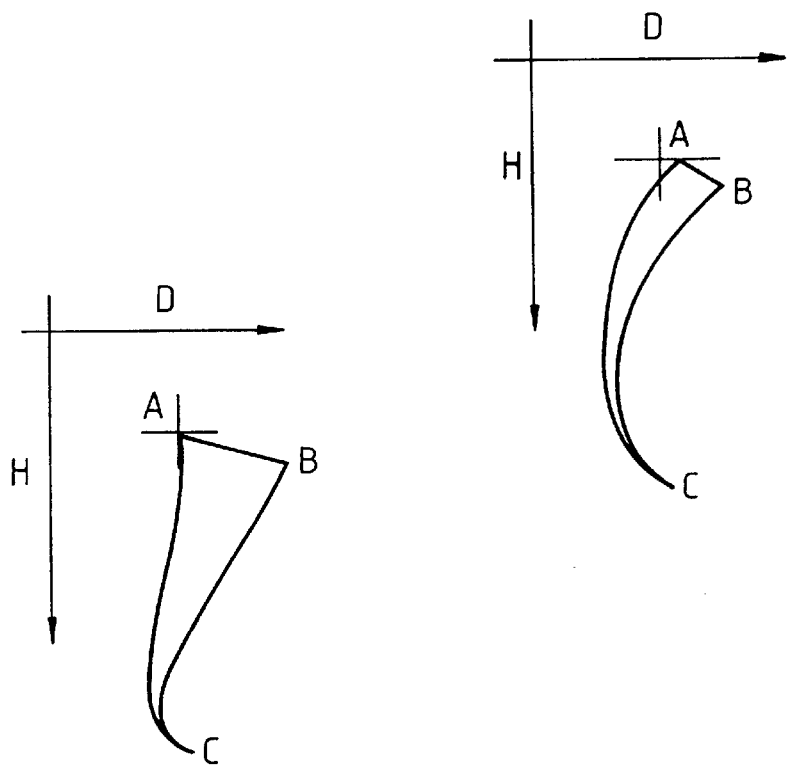
FIG. 30c

FIG. 32a
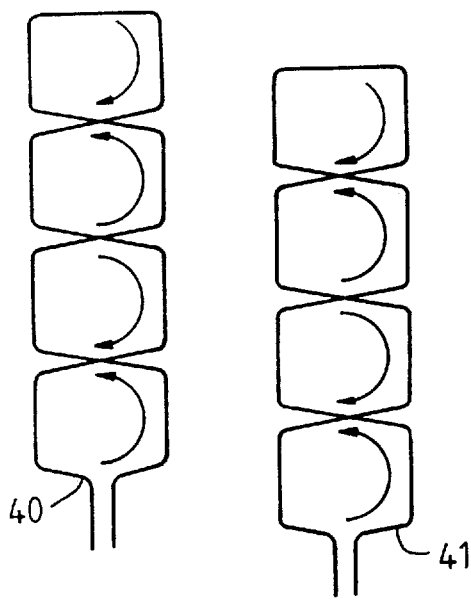
FIG. 32b
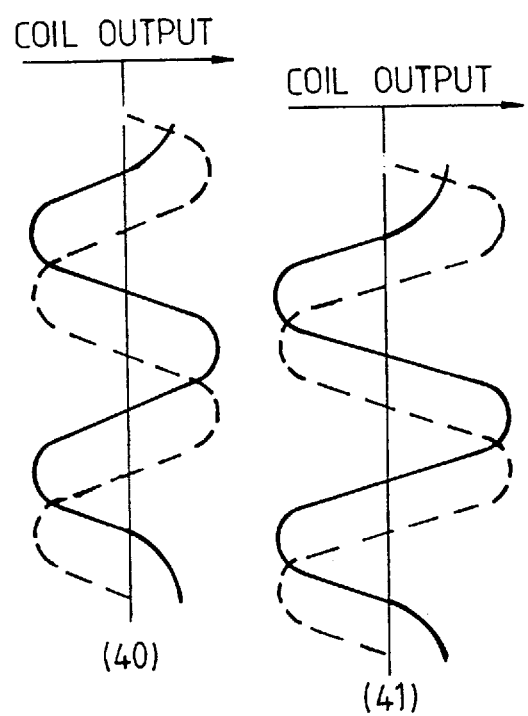
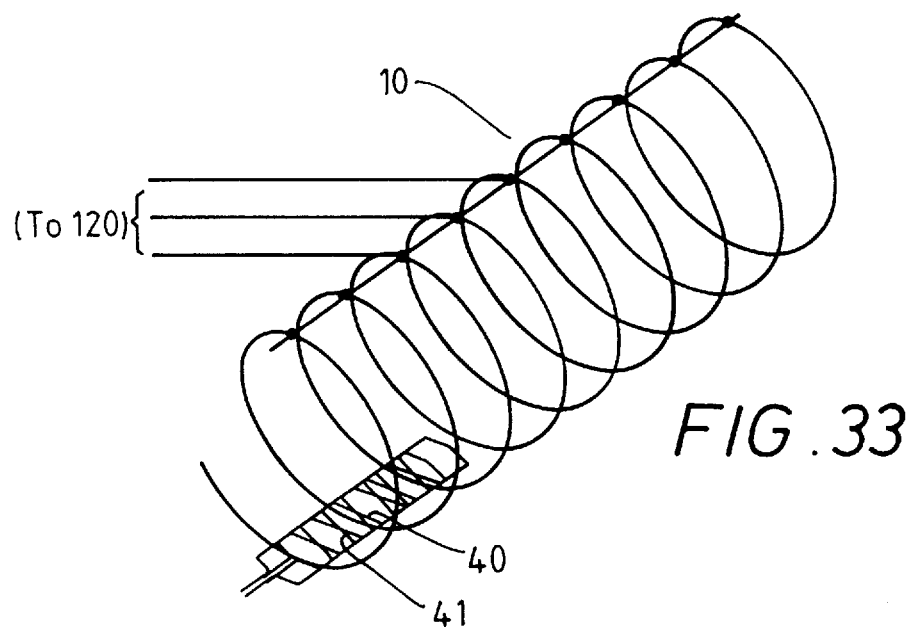
FIG. 33

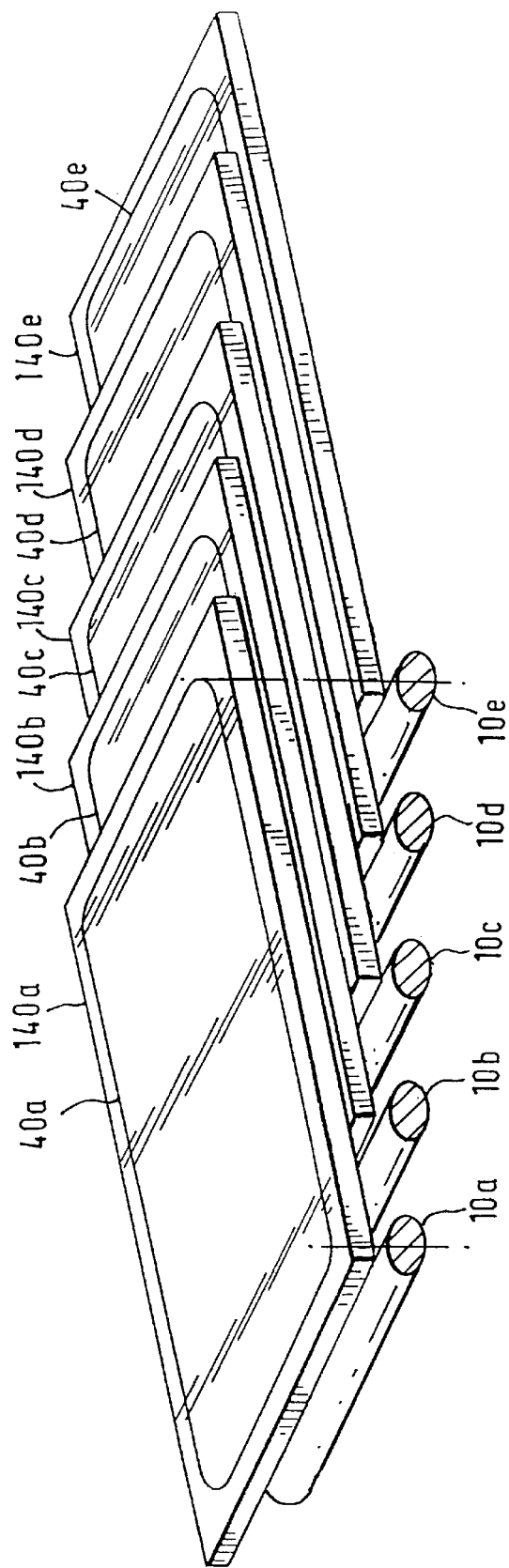

EDDY CURRENT PROBE SYSTEM AND METHOD FOR DETERMINING THE MIDPOINT AND DEPTH OF A DISCONTINUITY

FIELD OF THE INVENTION

This application relates to a probe for detection of flaws in materials, and to apparatus including such a probe. In particular, this invention relates to a probe for detection of cracks in structures; particularly, but not exclusively, for detection of cracks in submerged structures such as oil rigs, or in pipes.

DESCRIPTION OF THE BACKGROUND ART

One known non-destructive technique for testing the presence of cracks is alternating current potential drop (ACPD) testing, In which an alternating current is induced in the surface of a material to be tested and the interaction of the current with a defect is detected by a sensor. One type of eddy current testing system is described in British Patent GB 2012965B (U.S. Pat. No. 4,266,185), in which a pair of spaced contacting electrodes are engaged with an electrically conductive surface, and an alternating current is passed through the surface between the electrodes. A further pair of spaced apart pick up electrodes are used to measure a potential difference between two points on the surface. When a crack lies between the two points, the potential difference is higher since the current flows down one side of the crack and up the other; in either case, the distance traversed by the current is greater than the shortest distance between the two points. The voltage drop between the two points therefore provides a measure of the crack dimensions, as well as an indication of the presence of a crack.

A different type of probe is disclosed in GB 2225115A and corresponding U.S. Pat. No. 5,019,777. This probe avoids electrical contact with the surface and is therefore more reliable, and usable in underwater environments. In this proposal, there is provided a probe head which comprises a number of different sensors. The probe head comprises a solenoid coil which is fed with an alternating current, and a number of sensor coils. The solenoid coil induces eddy currents in the surface of a material to be tested, when brought into close proximity thereto. The sensor coils fall into two types. A first type comprises a coil wound round an axis parallel to the solenoid coil; these are referred to as "absolute" or "lateral" coils. The eddy currents flowing in the surface of the material induce a current in the lateral coils. The system of excitation (solenoid) coil, surface to be measured and lateral coil thus act as, respectively, the primary winding, core and secondary winding of a transformer and the magnitude of the voltage induced across the ends of the lateral coil varies with the resistance of the surface, and hence with the physical dimensions of any crack present. The output of such a coil can therefore provide a quantitative indicator of the depth of the crack In the surface. It may also be employed to measure the "lift-off" or separation between the probe and the surface as a function of the measured signal phase. However, because it is aligned with the solenoid, there is generally some direct induction from the solenoid, which can lead to inaccuracies. Also, the large dimensions of the lateral coil make it insensitive to the exact position of the crack, and consequently it is unsuitable on its own for determining the crack location and exact crack length.

For this purpose, a second type of sensor is employed comprising an elongate coil provided approximately coplanar with the surface to be tested, and consequently having an axis normal thereto (and to the axis of the solenoid). This coil is referred to as a "current perturbation coil". The current perturbation coil runs substantially the whole length of the solenoid, with its long axis aligned therewith, and is consequently symmetrically mounted about the centre, lengthwise, of the solenoid. Because its axis is normal to that of the solenoid, there is no substantial crosstalk from the excitation field and so the output is usually zero.

As will be discussed in greater detail below, the currents flowing in the surface of the material under test induce a current and voltage signal in a coil lying (or having a component lying) in a plane parallel to the surface. In the symmetrically mounted current perturbation coil of U.S. Pat. No. 5,019,777, when a symmetrical surface (either including or not including a flaw or crack) lies underneath the whole length of the magnetic field generated by the probe, the net signal output from the current perturbation coil is zero. However, if an end of a crack or flaw (or a change of depth) is present within the magnetic field of the probe, the current perturbation coil produces an output signal. Thus, the current perturbation coil produces a signal when either end of a crack or flaw is encountered, but not otherwise.

As will be discussed below, we have shown that the currents induced in the surface of the material rotate about centres underlying the ends of the solenoid, in opposite senses. At the centre of the solenoid, where the two contra-rotating currents meet, the current density is higher than that under the ends of the solenoid and beyond. There is thus a current gradient, having a maximum under the centre of the solenoid falling off towards the ends. For a very long solenoid, the current density may be constant over some regions, but there will be a gradient towards each end.

If a crack is present in the surface beneath the solenoid, as discussed above the current will journey down one side of the crack and up the other, and the associated material resistance leads to a voltage drop across the sides of the crack. However, we have realised that since the magnetic field, and hence current, varies along the length of the solenoid, where the crack is aligned with the solenoid axis the voltage drop caused will vary along the length of the crack, rising to a maximum under the centre of the solenoid. This voltage variation along the crack leads to local perturbation currents.

The perturbation coil used in the prior art is arranged symmetrically about the centre of the solenoid, so that the rise in potential difference along the crack underlying one half of the coil is matched by the fall in potential difference along the crack underlying the other half of the coil so that the generated perturbation currents are symmetrical and no net voltage across the coil is thereby generated, except when one end of the crack passes under the sensing coil. When this occurs, the voltage rise in one part of the crack is no longer compensated by a corresponding voltage fall along the other, so that there Is a net potential difference along the part of the crack underlying the perturbation coil, and hence a net perturbation current and a voltage is consequently generated in the perturbation coil.

Thus, in use, as the probe is moved over a surface, when one end of a crack is reached a pulse output voltage is produced by the perturbation coil, marking the start of the crack. As the probe moves along the crack, a signal indicating the crack depth is derived from the lateral coil. When the other end of the crack is reached, a further pulse is generated by the perturbation coil. By logging the outputs of the two coils, the start and end points of the crack, and hence its length, together with its depth may be accurately measured.

SUMMARY OF THE INVENTION

We have, however, discovered that an equally accurate probe may be provided by making use of the variation of the induced current along the length of a crack, to provide a direct measure of crack depth as well as a sensitive measure of the crack start and end positions. This is possible because the depth of the crack, and hence the resistance between the two sides of the crack, not only affects the voltage drop across the crack but also the magnitude of the voltage gradient and hence potential difference along its length.

Accordingly, in one aspect, the invention provides a probe comprising means for inducing a current in a material surface, said current being arranged to run across the direction of a crack therein, and to exhibit a different value at different points along the said crack, and means for providing a signal corresponding to the potential difference along said crack caused thereby, and for deriving therefrom an indication of the depth of said crack.

In one embodiment, the means for inducing a current comprises means for inducing a current gradient, and this may be a solenoid coil as discussed above. In such an embodiment, the sensing means may comprise a coil approximately coplanar with the surface, positioned asymmetrically with respect to the centre of the length of the solenoid. An embodiment of the invention provides a coil including a twist, so as to form an "8" closed shape, disposed about the longitudinal centre of the solenoid, so as to be effectively antisymmetrical.

In a different aspect of the invention, we provide means for measuring the depth of the crack by sensing the current perturbation in the surface of a material including the crack. The means for measuring the current perturbation may comprise current sensors positioned in portions of a field exhibiting an asymmetrical gradient, for example either an asymmetrically positioned coil or coils, or a figure of "8" wound coil, or alternatively means for measuring the vertical fall off of perturbation current from the surface (for example, at least two sensors positioned at different vertical distances from the surface, for example a pair of coils, connected in opposition one to the other).

In the above aspects, the invention provides a probe which is less sensitive to variations in "lift-off" or separation from the surface under measurement than the "absolute" coil of the prior art, and furthermore may be provided in a more compact assembly since it may be substantially coplanar with the surface under measurement rather than requiring large "absolute" or lateral coils transverse to the surface. Some embodiments appear also to exhibit less sensitivity to electrical noise.

A further problem of the prior art is that the measurement of distance or position of a flaw or crack is based upon a time measurement and an assumption of constant probe speed. This assumption is often wrong due to human error. Manually moved probes can thus be inaccurate and slow to use. Accordingly, in a further aspect, the invention provides a probe array for measurement of surface flaw comprising means for generating a magnetic field or fields extending in at least one dimension and sensor means spaced along within the magnetic field or fields, and means for reading out said sensor means. In submarine or similar hazardous environments, such a system can be considerably more accurate than a probe moved by a human diver.

It is known from U.S. Pat. No. 3,875,502 to provide a probe comprising a single excitation coil and a plurality of sensor coils which are separately read out in sequence to provide a scan. In a preferred embodiment of this aspect of the invention, however, we provide a probe system comprising a magnetic field generator which comprises a plurality of independently energisable portions, and sensor means extending coterminously with the magnetic field generator. The sensor means preferably comprises a plurality of portions having a localized response. The different portions of the magnetic field generator are preferably sequentially energised, and the sensor is read to provide a reading corresponding to the region of the surface at which the localised magnetic field produced by the energised portion is located. By providing a localised magnetic field which is sequentially provided at a number of different points, along the surface, the effects of crosstalk from adjacent fields on localised parts of the sensor arrangement are substantially reduced or avoided. Furthermore, the readout lines from the sensors may be simplified; for example, there may be a common readout line for a plurality of separate sensors, or the sensor arrangement may comprise a single elongate sensor having a cyclically or periodically varying sensitivity connected to the single readout line. Thus, a single readout line can be employed without requiring multiplexing of the sensor outputs, thus reducing the likelihood of corruption of the signal from the probe to an analysing or logging unit. Finally, because only a localised magnetic field is generated at any particular time, the amount of current required to generate the field may be reduced as the inductive resistance may be lower.

In another embodiment, the sensor arrangement of the array comprises flat coils coplanar with the surface, of the type discussed in the first aspect of the invention above; this enables a less bulky arrangement than an equivalent arrangement employing "lateral" coils.

In another embodiment, the probe array is provided as a flexible sheet which can be laid over the surface to be tested, to conform to the shape thereof. This enables the use of the same probe in a number of different environments or on different paths of a structure, without wide variations in liftoff. Preferably, the sensors are perturbation current sensors according to the above embodiments, for example sensors mounted asymmetrically within the magnetic field generated by each generator.

According to a further aspect of the invention, there is provided a probe comprising a magnetic field generator and an induced current sensor, in which the arrangement is such that the probe may be switched to operate in a plurality of different modes, in which the sensor generates signals which are differently related to the presence and/or dimensions of a flaw, comprising A pair (or more) of magnetic field generators, the arrangement being such that energising different generators or combinations of generators changes the relative position of the sensor to the magnetic field generated; for example, to change the position from lying symmetrically within the magnetic field to lying asymmetrically therewithin. In this way, a single sensor can function either as a conventional "current perturbation" type sensor responsive only to the ends of cracks or as a sensor giving a measurement of crack depth; but these modes of operation are of course not exhaustive. Thus, a limited number of sensors and sensor readout lines can be used to provide a larger amount of data. Production is also simplified, since fewer different types of sensor need be made. Communication between the probe and the analysis or logging unit is also improved, since the number of separate signalling lines, or multiplexers, is reduced. This aspect of the invention Is conveniently employed in a probe array according to the preceding aspect of the invention.

Other aspects and preferred embodiments of the invention are as described or claimed hereafter.

BRIEF DESCRIPTION OF THE DRAWINGS

The invention will now be illustrated, by way of example only, with reference to the accompanying drawings in which:

FIG. 8 shows schematically the alternating magnetic field produced by the probe of FIG. 6 or FIG. 3;

FIG. 9a shows the voltage induced in a coil passing through the field of FIG. B;

FIG. 9b shows the integral of the induced voltage of FIG. 9a, corresponding to the magnitude of the magnetic field of FIG. 8;

FIG. 10 is an elevation showing the probe of FIG. 6 aligned with the plate of FIG. 1a;

FIGS. 19a and 19b are respectively a sectional end elevation and a semi-sectional front elevation showing this embodiment in yet greater detail.

FIGS. 22a and 22b shows schematically sectional views showing alternative connection states of a third embodiment of the invention; and FIGS. 23a and 23b show corresponding outputs of that embodiment in response to a detected defect;

FIG. 24 shows a schematic section elevation of a fourth embodiment of the invention;

FIGS. 25a and 25b are respectively front and side elevations of an alternative embodiment to that of FIG. 24; and FIG. 26 shows a detail of FIG. 25;

FIGS. 30a–c illustrate a method of signal processing for use with probes according to the invention.

FIG. 32a shows schematically an alternative sensor arrangement to that of FIG. 31; and FIG. 32b shows schematically the sensivity with position of the arrangement of FIG. 32;

FIG. 33 shows schematically a perspective view of an embodiment including the sensor arrangement of FIG. 32a;

FIG. 37 shows schematically the arrangement of sensors in a further embodiment of the invention based upon that of FIG. 32a;

FIG. 39b is a section plan view corresponding to FIG. 39a;

FIG. 40 is a sectional part view showing an arrangement providing a flexible scanning probe according to an embodiment of the invention.

EDDY CURRENT CRACK DEPTH MEASUREMENT

Figure 1A:
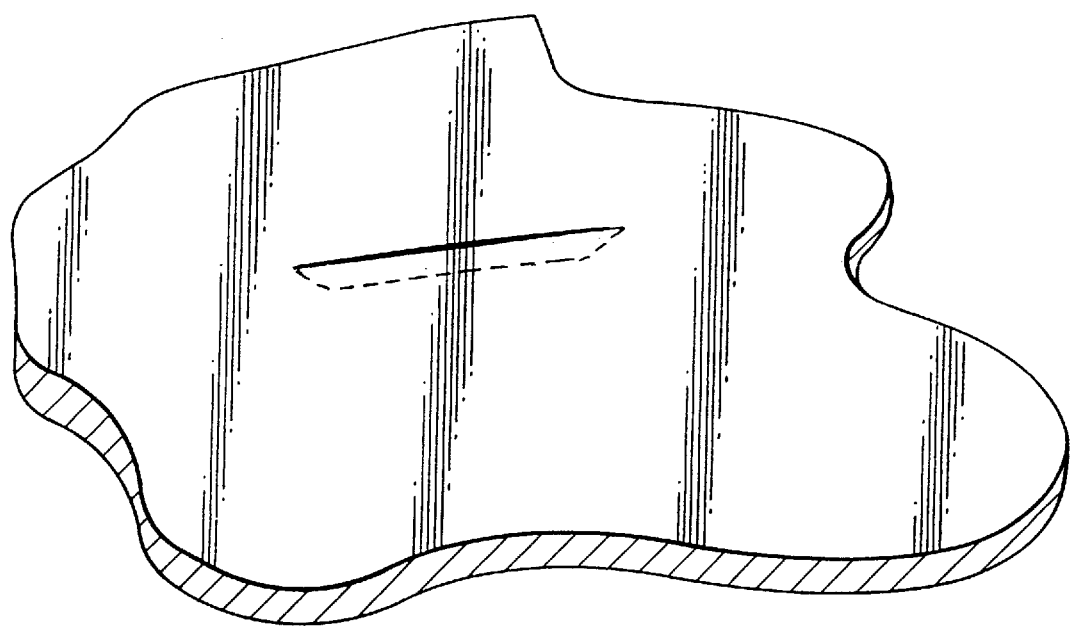
FIG. 1a shows schematically a perspective view of a crack in a plate.

Referring to FIG. 1a, a surface breaking crack is shown in a plate. The crack acts as a stress concentrator, and the presence of a crack therefore increases the stress in the uncracked part of the plate (or other structure). A common source of cracks in metal structures is at welded joins, where the welding process can embrittle the welded parts. When a stress greater than a critical level, which is dictated by the dimensions of the crack (generally its depth) is applied to a cracked part, the crack propagates rapidly and failure occurs. Iron and steel structures such as ships and oil rigs, destined for immersion in relatively cold water at which they are brittle, can thus fail catastrophically at welds. Other typical welded or other metal structures in which failure due to cracking is a problem are, for example, pressure vessels for chemical process plants and pipelines (particularly pressurised pipes).

Non-destructive techniques of crack detection are preferred, for obvious reasons. One such method employs currents induced in the surface of the material.

Figure 1B:
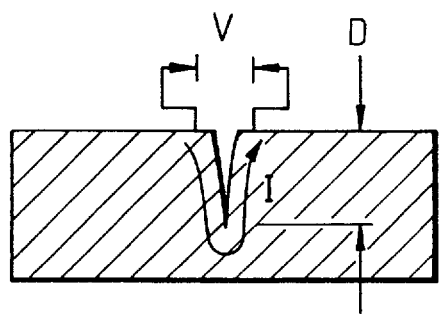
FIG. 1b shows schematically a cross-sectional view through the plate across the line of the crack with surface current and voltages shown.

Referring to FIG. 1b, which shows a section through the crack in the plate in FIG. 1a, in AC crack detection, a current is generated in the surface of the plate (e.g. by inducing eddy currents, as in GB 2225115). Away from the ends of the crack, the current generally flows down one side of the crack and up the other, so that to traverse the distance between the two sides of the crack the current travels the distance 2D (where D is the crack depth). In portions of the plate in which there is no crack, of course, the current need travel only a much smaller distance directly over the surface. The potential drop between points at either side of the crack is, by Ohms law, the current multiplied by the resistance of the current path, which is the surface resistivity R of the plate multiplied by the length of the path. Thus, the potential difference across the crack is 2DRI. From a knowledge of the material of the plate and of the magnitude of the current, the crack depth D is thus readily derived by measuring the potential difference across the crack.

It is desirable to test welded structures at periodic intervals, as new cracks can be generated by impacts, and cracks can grow under fatigue, static fatigue or stress corrosion. However, testing every welded joint in a complex structure such as, for example, an oil rig is a major undertaking and since submerged parts are dark, and divers are hampered by diving suits and may be unable to remain submerged for extended periods of time, it is particularly important in such applications to use simple, robust and reliable means for crack detection and crack depth measurement.

GENERAL DESCRIPTION OF MEASUREMENT SYSTEM

Figure 2:
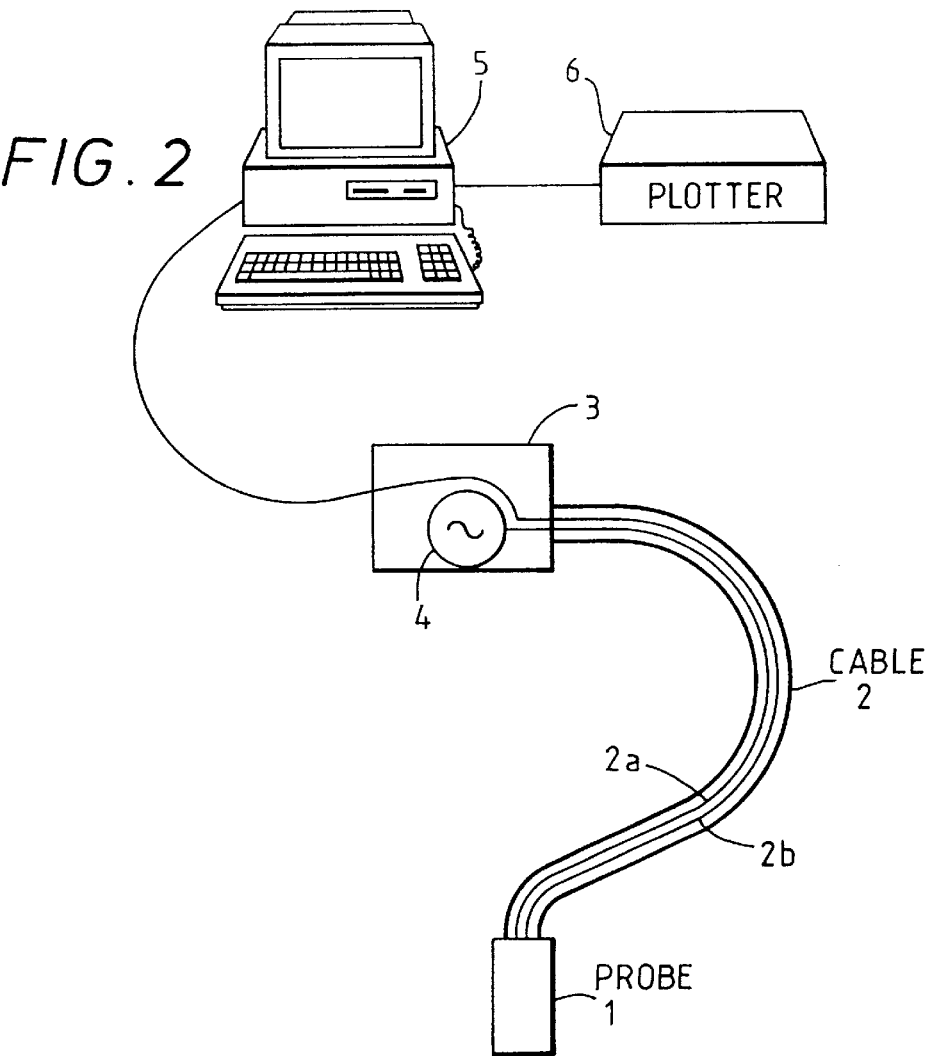
FIG. 2 shows schematically a crack detection, measurement and logging system.

Referring to FIG. 2, the general elements of the crack detection and measurement system provided in GB 2225115A (U.S. Pat. No. 5,019,777), which are applicable also to embodiments of the present invention, will now be discussed.

A crack measurement and detection system for use, for example, in measuring defects in oil rig structures comprises a probe 1 of a size and shape to be hand holdable by a diver, connected via a flexible cable 2 to a probe driving unit 3 typically located above water level. The cable 2 includes signal lines 2a which carry the crack detection/measurement signals from the probe, and power supply lines 2b which carry an AC energising current from an AC power supply 4 located in the driving unit 3 to the probe 1.

The signal from the signalling lines 2a may be plotted, logged or monitored in any way, but it is convenient to provide a data analysis unit 5 which typically comprises a digital processor such as a personal computer and an analogue-to-digital converter (not shown) for converting the analogue signal from the signalling lines 2a into a form to be analysed. A plotter 6 may be connected, if desired, to the analysis unit to produce permanent output traces.

In portable applications, the AC power supply 4 may be co-located in a unit with the analyser 5.

Figure 3:
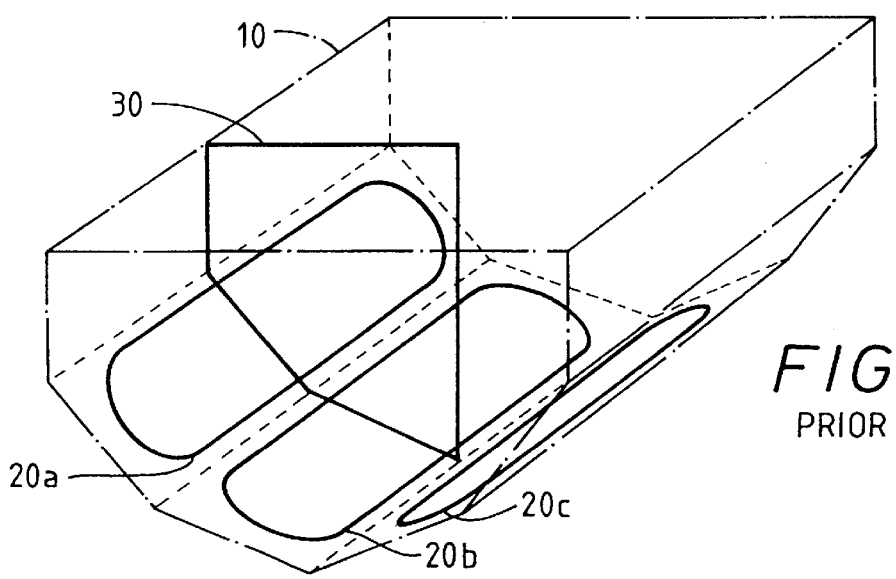
FIG. 3 shows schematically a known probe forming part of such a system.

Referring to FIG. 3, the probe unit 1 of GB 2225115 is shown in greater detail. It comprises a plurality of coils each comprising a plurality of windings of conductive metal wire, wound typically on to a former (not shown) and encapsulated in polymeric resin so as to be sealed against the ingress of water or atmospheres. A first coil 10 comprises an elongate solenoid energised from the AC power lines 2b, for example at 40 kHz using 250 mA peak-to-peak. The plane in which the windings are wound is normal to the long axis of the probe 1. The coil is formed on a multifaceted prism former, having a convex lower face. Each facet of the lower face therefore comprises an elongate rectangle running lengthways along the probe 1. Disposed on several of the facets are flat rectangular coils 20a, 20b, 20c, running substantially the length of each facet and being symmetrically positioned within the length of the facet. The plane of the windings of each of the facet coils 20a–20c Is thus normal to that of the windings of the solenoid excitation coil 10. The ends of the coils 20a–20c are connected to signalling lines 2a; one end of each may be connected to a common line.

Also provided are several coils 30 ("absolute" or "lateral" coils) the planes of the windings of which lie parallel to that of the excitation solenoid coil 10. For clarity, only one such coil is shown. The ends of these coils, as with those of the coils 20a–20c, are connected to signalling lines 2a.

Figure 4:
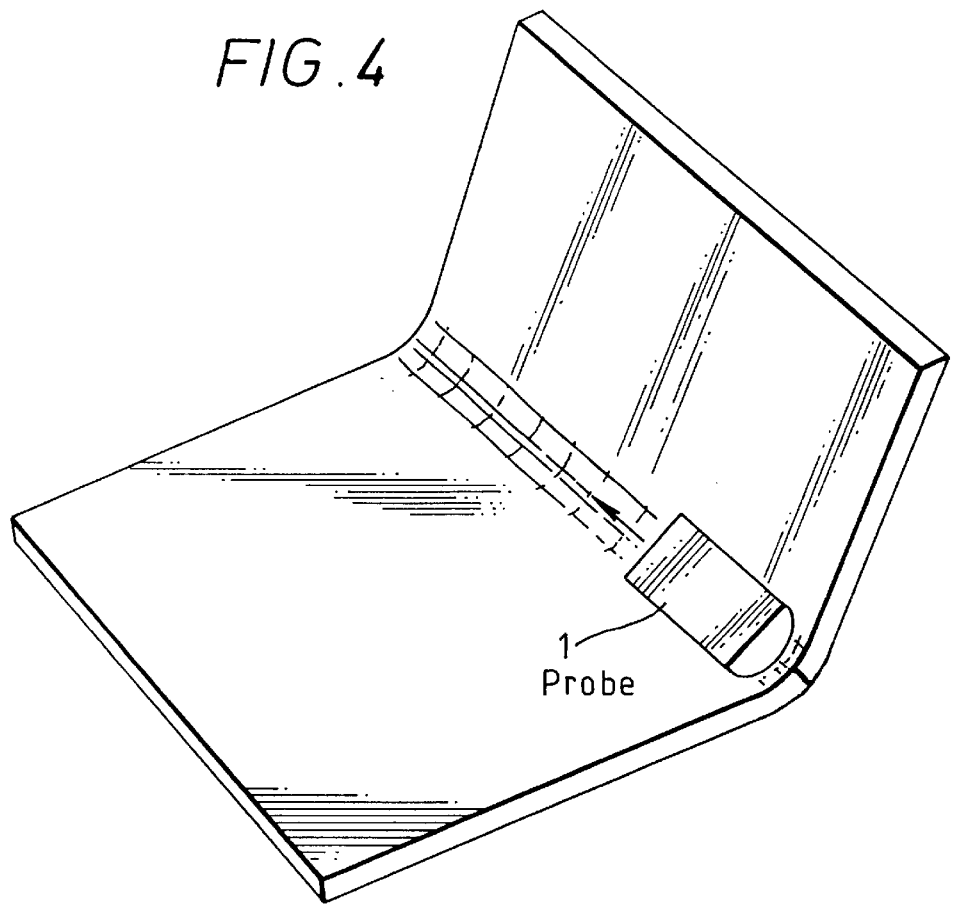
FIG. 4 shows schematically the method of use of the known probe in examining weld defects.

Referring to FIG. 4, in use, a human operator grasps the probe 1 and moves the probe at a substantially constant speed (so far as he can judge) over a surface to be scanned for cracks. The facets of the probe lower face are designed to cooperate approximately with the curvature of a weld between two plates as shown in FIG. 4, since it is at such welds that cracks often develop. The facets will therefore generally lie roughly parallel to the surface of the weld. The excitation coil 10 generates eddy currents in the surface of the weld area, and the sensor coils 20, 30 generate respective output signals which are periodically read by the analyser 5, from the output of which the occurrence and dimensions of cracks can be determined. Periodically, the diver may indicate a position along the weld to enable the positions of the cracks to be accurately monitored; for example, via his voice communication channel.

Figure 5:
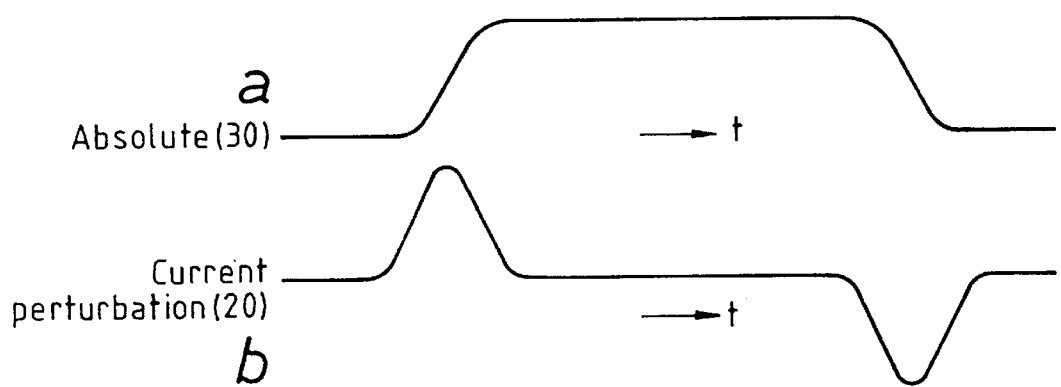
FIG. 5 shows schematically output signals generated by the probe of FIG. 4 in use as it passes over a crack.

Referring to FIG. 5, the output signals plotted by a plotter 6 (derived as discussed below) corresponding to the magnitude of the AC signal outputs of the coils 20 and 30 are shown as the probe 1 is moved over a crack; because of the linear probe speed, the time axis also represents distance. The diagrams are not to scale. Referring to FIG. 5a, it will be seen that the output of the coil 30 rises gently from a normal (null) value to a higher value which is related to the depth of the crack, while the crack lies beneath the probe 1. Referring to FIG. 5b, the output of the coil 20, on the other hand, provides a peak when either end of the crack is under the probe 1 but lies at the same (null) level when the probe is over the middle of a crack as when it is not; the peaks at the ends of the crack are in opposite senses, and the sense of a peak depends upon the direction in which the probe is moved.

The magnitude of the signal from the sensors 20, 30 or 40 is affected not only by the crack depth but also by the separation between the probe 1 and the surface to be measured (known as the probe "lift-off"). Variations in the depth of a coating on the surface, or protruberances on the surface, may cause the lift-off to vary as the probe 1 is manipulated over the surface by an operator. Accordingly, it may be desirable to provide a measure of the lift-off during operation and to correct the signals output from the sensors using the measurement.

In the prior art, the lateral or absolute coil 30 functions, as noted above, somewhat like the secondary winding of a transformer and is correspondingly coupled to the excitation coil 10 via the conductive surface which acts as the core. The separation from the surface varies the inductance exhibited, and consequently changes the phase angle between the signals supplied to the excitation coil 10 and that derived from the absolute coil 30. Accordingly, the lift-off or separation can be measured by measuring the phase angle or the imaginary part of the AC output signal (referenced against the AC excitation signal). It is found that the same technique can be employed to derive a measure of lift-off from the output of the coil 40 positioned according to the invention. The analyser 5 is accordingly arranged to derive a measure of the lift-off from the probe output signal.

SIGNAL PROCESSING

Accordingly, the analyser 5 may for example be arranged to analyse the probe outputs by deriving real and imaginary parts of the (notional) AC impedance obtained by referencing the signals received from the signal lines 2a against the energising signals transmitted on the power lines 2b. The real and imaginary pair of values is then processed by applying predetermined transformations in the complex impedance plane, and the real part of the transformed signal in plotted as a direct measure of crack presence or depth. The imaginary part may also be plotted as a measure of liftoff.

The object of the transformations is therefore to convert the real and imaginary impedence values provided from a measuring coil (or phase and amplitude values, if required) into defect and separation or liftoff signals, such that variations in liftoff and presence or size of defects are separated and the defect signal is unaffected by liftoff alterations in use. This corresponds to the ideal plot shown in FIG. 30a, in which after transformation the defect values derived will lie along the locus A-B, and liftoff signals will lie along the locus A-C, the two locii being orthogonal so that the signals are completely separated.

Figure 34:
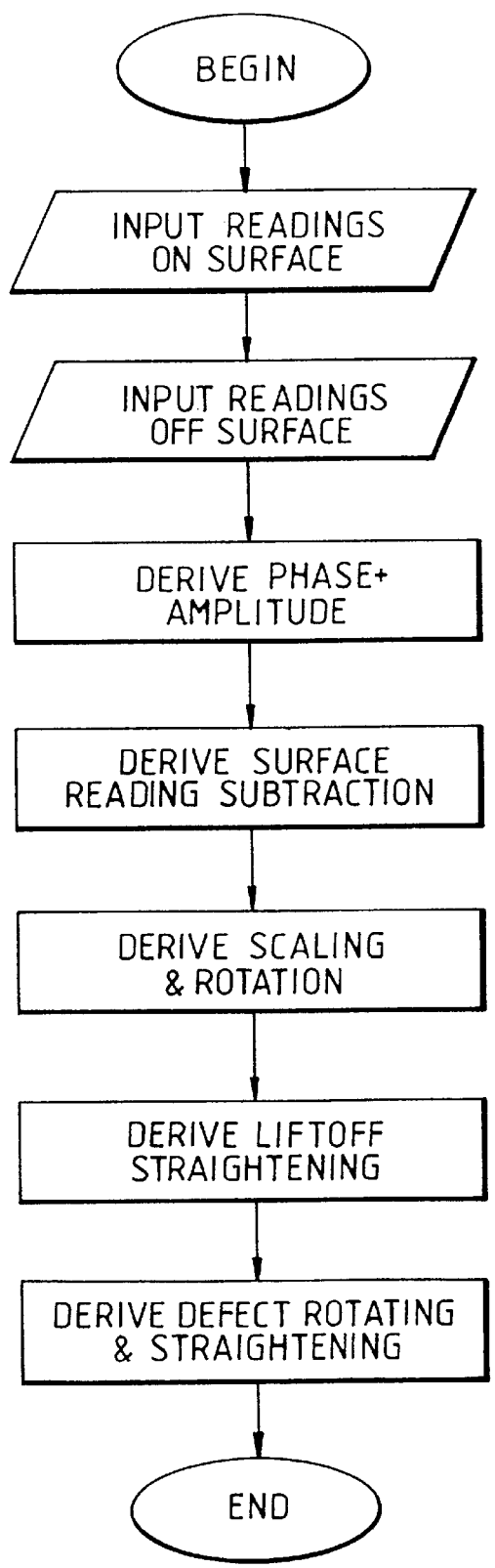
FIG. 34 is a flow diagram showing schematically the process of an initial signal processing stage for processing signals derived from a probe according to the invention.
Figure 35A:
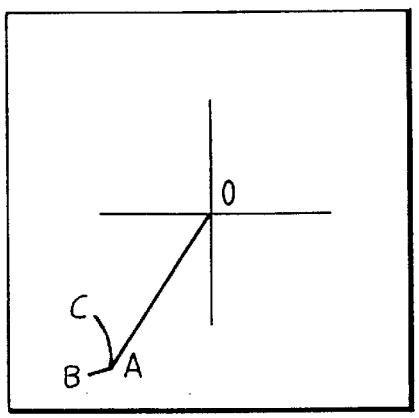
FIGS. 35a–f are graphs showing schematically the effects of the signal processing stages of FIG. 34.

Referred to FIGS. 34 and 35, the transformations required are derived, in an initial phase, as follows. Firstly, the probe is placed close to the surface to be measured, and the output of the signal lines 2a are read, and analysed by reference to the amplitude and phase of the energising signals transmitted on the power lines 2b, to produce real and imaginary complex impedance components (phase and amplitude could be used instead, however). These are plotted as the point A in FIG. 35a. Next, the operator positions the probe at a number of points at successive spacings away from the surface to be measured, to a point distant from the surface, For each spacing, as above, the signal from the signal lines 2a is referenced against the energizing signal to derive real and imaginary impedance components, which are as shown in FIG. 35a along the locus A-C, where C corresponds to the point distant from the surface.

Next, the probe is placed over a point where a defect is known to exist (for example a slot on a test plate) and a measurement is taken. The real and imaginary components of the signal measured on the signal lines 2a is shown in FIG. 35a as the point B.

Figure 35B:
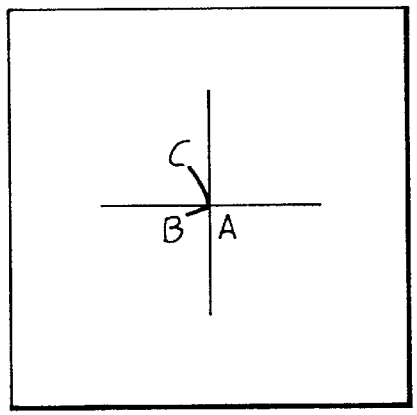

The real and imaginary values of the point A (corresponding to a normal probe output reading) are stored at a subtractive correction. The effects of subtracting these coordinates from the locii A-C, A-B is shown in FIG. 35b.

Figure 35C:
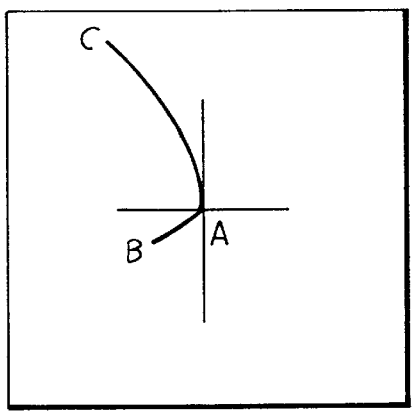
Figure 35D:
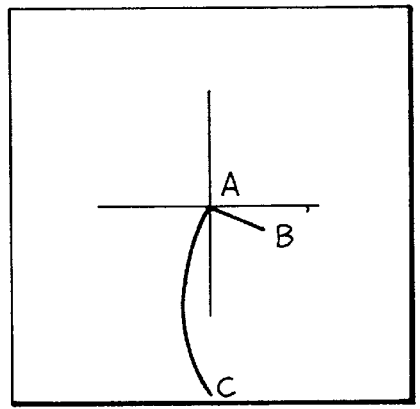
Figure 35E:
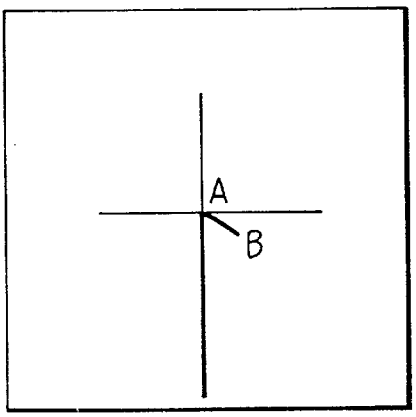
Figure 35F:
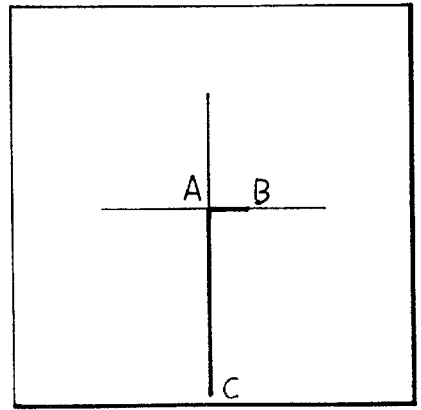

Next, a normalising scaling factor is calculated so that, when multiplied by the scaling factor, the length of the straight line connecting A and C is equal to a predetermined constant. The effect of this is illustrated in FIG. 35c. Next, a rotational transformation is calculated such as to rotate the point C to lie on the lower half of the imaginary coordinate axis (as illustrated In FIG. 35f). This rotation transformation may be combined with the scaling transformation and the translational (subtractive transformation) to provide a single two dimensional transformation defined by transform coefficients stored in the analyser 5. The above steps are used in the prior art.

According to a preferred embodiment, further transformations are derived; firstly, by deriving coefficients to effect a straightening operation; for example, a quadratic is fitted to the measured points along the locus A-C, and the transformation necessary to map the points from the locus on to the imaginary axis is calculated. The effect is shown in FIG. 35e. Likewise, the transformation necessary to map the locus A-B on to the real axis is calculated; the effect is as illustrated in FIG. 35f. These last two steps further reduce the interaction between liftoff and defect measurements, so that the measurement of defects becomes less sensitive to the spacing at which the probe is located from the surface.

Figure 36:
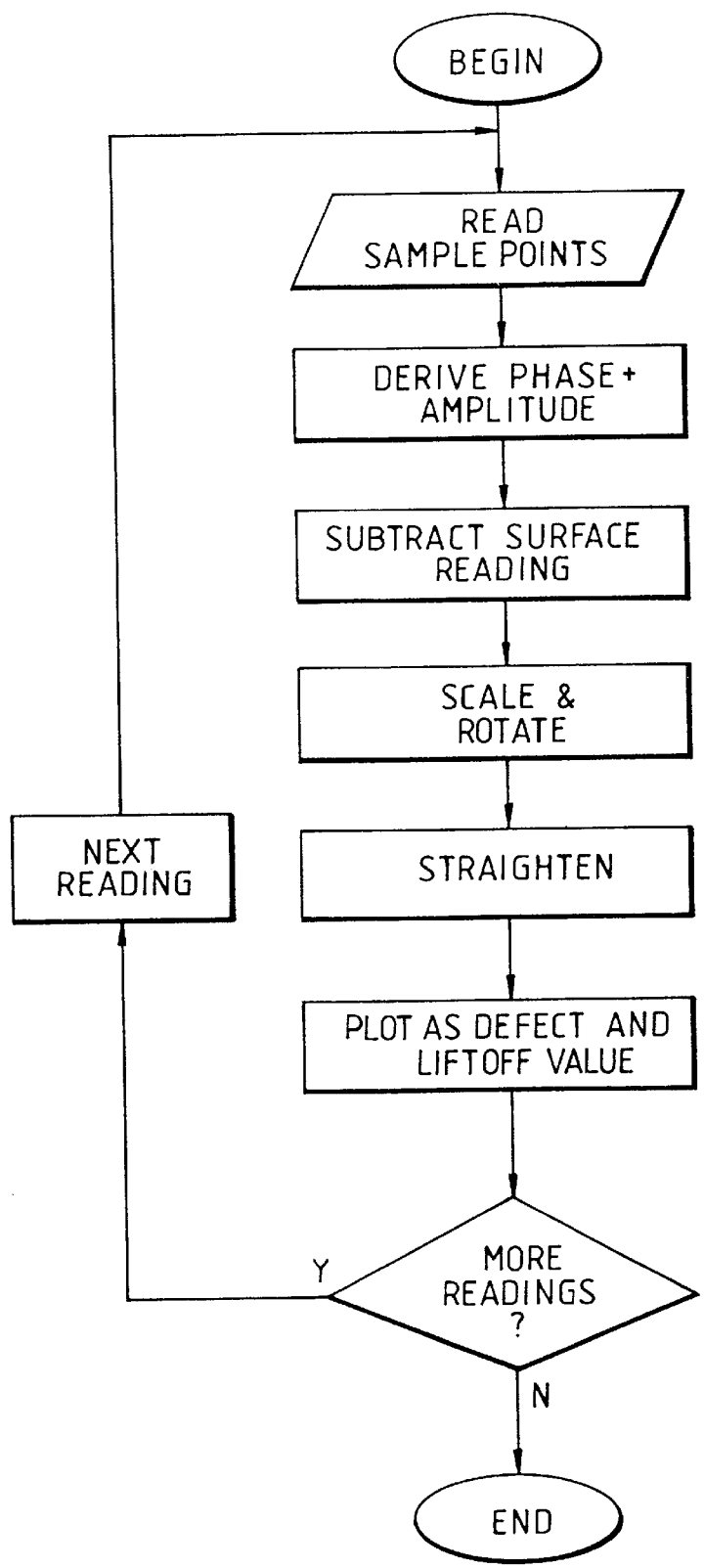
FIG. 36 is a flow diagram showing schematically the signal processing which may be applied to a signal from a probe according to the invention.

Having calculated a transformation or transformations to be applied to real and imaginary components from a probe output to translate, scale, rotate and separate the components thereof, each (real, imaginary) or (amplitude, phase) coil reading coordinate pair can then be converted to a pair of defect and liftoff signals, to be plotted or subsequently processed, as shown in FIG. 36.

The analyser 5 may comprise a hardware phase sensitive detector, or alternatively the signal output by the probe may be sampled in excess of twice the energizing frequency and the real and imaginary components may be derived by digital calculation.

Referring to FIG. 30b, employing the output of the absolute coil described in the probe of GB 2225115A, it will be seen that even after processing according to the prior art stages illustrated in FIG. 35(a)–(d) to reduce the interaction between lift-off and flaw depth is performed, the resulting signal locii diverge from the ideal shown in FIG. 30a and, in particular, the line segment AB is not particularly horizontal and the line segment AC deviates significantly from the vertical, and both are curved. Further, the range of defect signal (the length of the line A-B) is small.

However, a signal produced by a probe according to embodiments of the invention is, as shown in FIG. 30c, more similar to the ideal output shown in FIG. 30a. The subsequent processing of FIG. 30e and FIG. 30f further reduces the interaction between liftoff and crack depth.

GENERAL PRINCIPLE OF THE PREFERRED EMBODIMENTS

Figure 6:
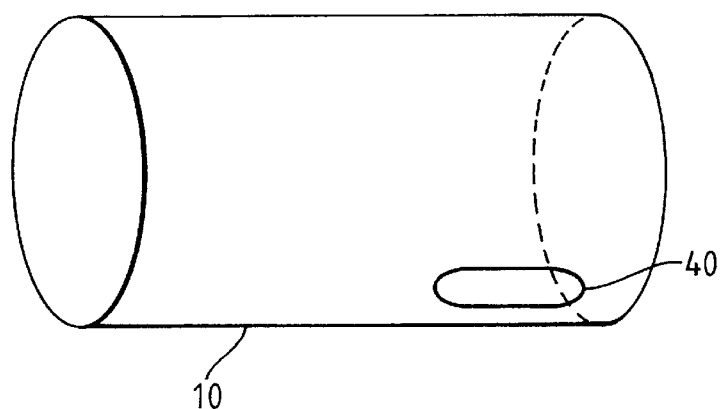
FIG. 6 shows schematically the elements of the probe according to one embodiment of the invention.

Referring to FIG. 6, in one exemplary embodiment of the invention, a probe 1 comprises an elongate excitation solenoid coil 10 and, disposed at or nearer an end thereof, a flat sensor coil 40 the plane of which is normal to that of the windings of the excitation coil 10.

Figure 7:
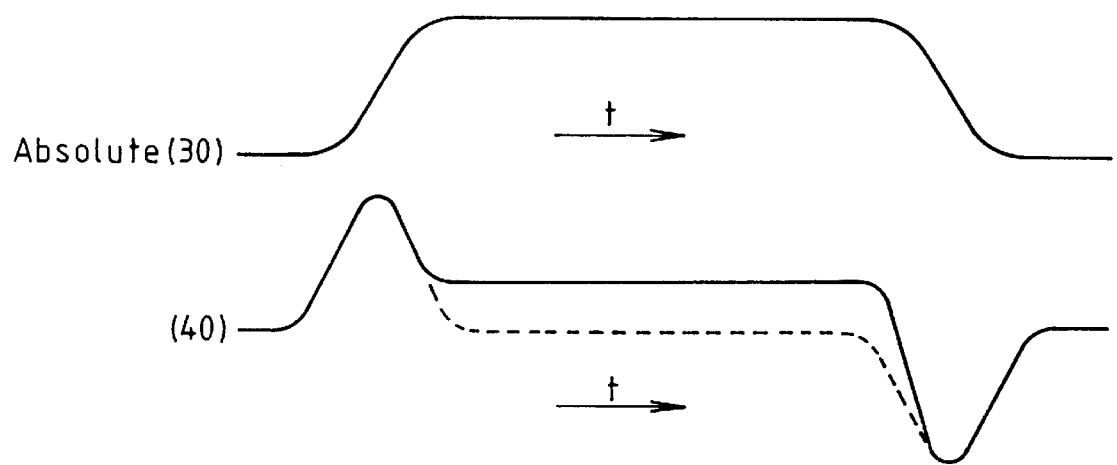
FIG. 7 shows schematically output signals produced by the probe of FIG. 6 in a form corresponding to those of FIG. 5.

Referring to FIG. 7, which corresponds to FIG. 5, FIG. 7b shows that the output of the coil 40 includes a non zero level when the probe lies over a crack, when compared to FIG. 5b in which it does not. We have found that varying the position of the coil 40 along the length of the excitation coil 10 varies the magnitude of this offset signal level and also the heights of the two end peaks. When the coil 40 is positioned symmetrically in the middle of the excitation coil 10, a signal similar to that of FIG. 5b can be obtained whereas at other positions, a signal similar to that of FIG. 5a can be obtained. As will be discussed below, other geometries than that of FIG. 6 can be used to acheive this effect.

The reasons for this behaviour will now be discussed. FIG. 6 shows the magnetic field generated by the excitation coil 10. The field shown corresponds to a coil having a constant spacing between each winding, and a constant cross section along the winding axis, and a former with a relative permeability close to unity (rather than an iron core, for example).

It will seen that the magnitude of the radial magnetic field at the outer surface of the coil varies along the axial length of the coil. The profile of the variation of the field depends upon the geometry of the coil (for example the ratio of the diameter to length of the coil, and generally also the cross-sectional shape).

When such a coil is energised by an alternating current, an alternating field is produced with the probe as shown in FIG. 8 and described above. If the energised coil is brought into close proximity with the surface of an electrically conductive plate, an electrical field conforming to the profile at the magnetic field will be created within the plane of the surface of the plate but with Its direction normal to the magnetic field. This electric field will cause current to flow upon the surface of the plate; If the field alternates at a suitable frequency, the current flows are confined to a surface layer of the plate. For example, at an excitation of 40 kHz, at a suitable energising current level, the current flow in the surface of a mild steel plate is confined to the surface 0.1 mm layer.

The induced current will have a profile which corresponds to the field profile generated by the coil. The current profile therefore also follows a gradient along a line in the surface lying under the coil.

Referring to FIG. 9a, this may be experimentally varified by moving a small flat search coil across the surface of a conductive plate beneath such a coil in close proximity thereto; the output current or voltage signal from the coil is shown in FIG. 9a. This current induced in the search coil is effectively the differential (with respect to distance) of the current flowing in the conductive plate, so that the integral (with respect to distance) of the search coil output will show the magnitude of the current field flowing in the conductive plate; as shown in FIG. 9b, the current flowing in the plate is null a substantial distance away from the excitation coil 10, rising through a substantial level at the ends of the coil to a maximum in the centre of the coil, and is symmetrical in magnitude about the centre of the coil.

Figure 10A:
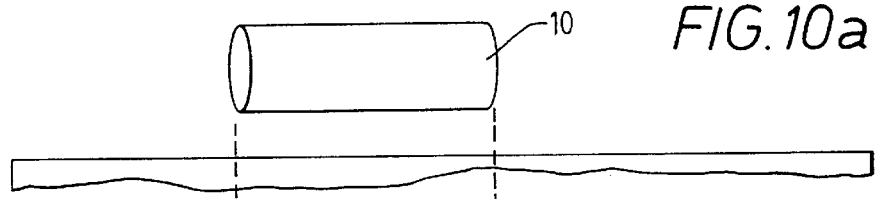
Figure 10B:
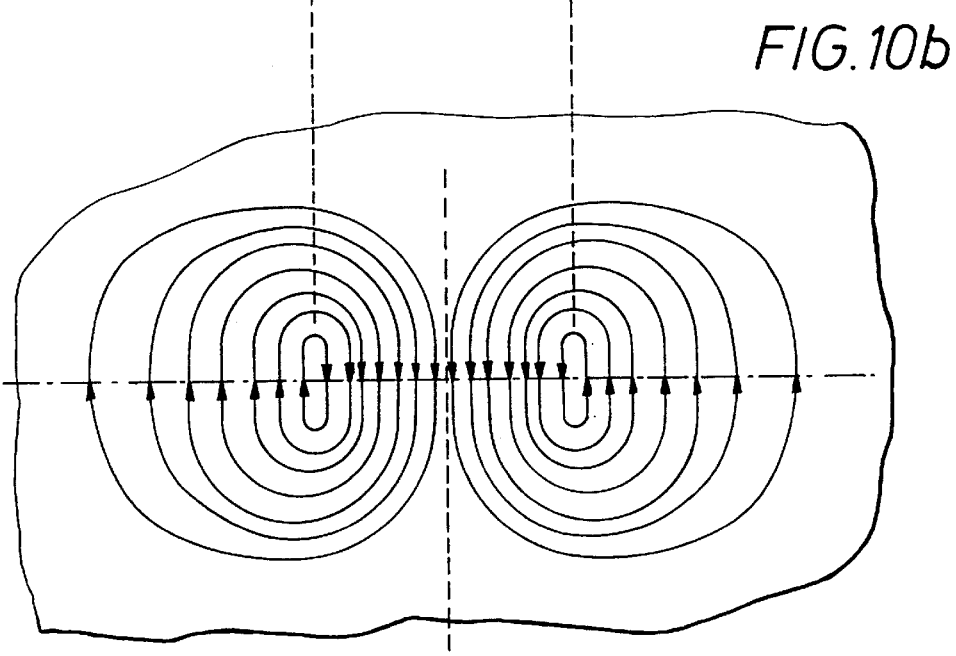
FIG. 10b is a corresponding plan view, omitting the probe, showing the circulating currents induced in the surface by the magnetic field.

Referring to FIG. 10a, a side elevation showing the solenoid excitation coil 10 overlying a conductive plate is shown. Referring to FIG. 10b, the circulating current flow contours within the surface of the conductive plate below the coil 10 are shown in plan view. It will be seen that the current flows in two contra-rotating eddies each centred about a point underlying (at least approximately) an end position of the solenoid 10. The maximum current density is, as noted above, under the centre of the solenoid 10.

Figure 11:
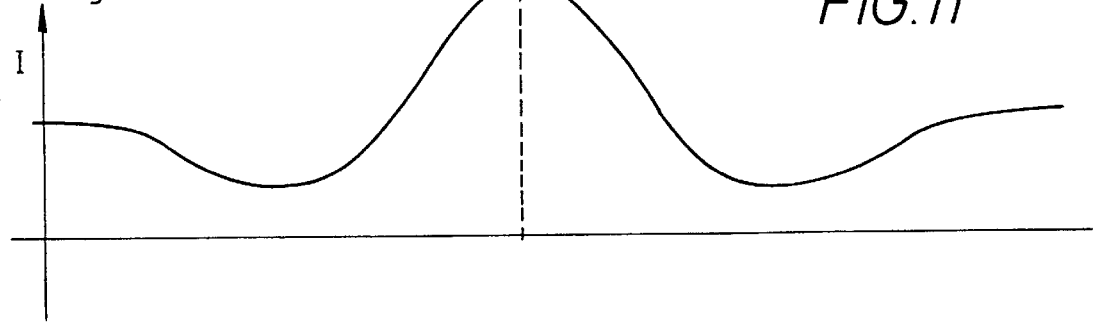
FIG. 11 is a corresponding graph of the intensity of a current along a line in the plate lying beneath the axis of the probe.

Referring to FIG. 11, the intensity of current crossing the central line underlying the axis of the solenoid 10 is shown.

Figure 12:
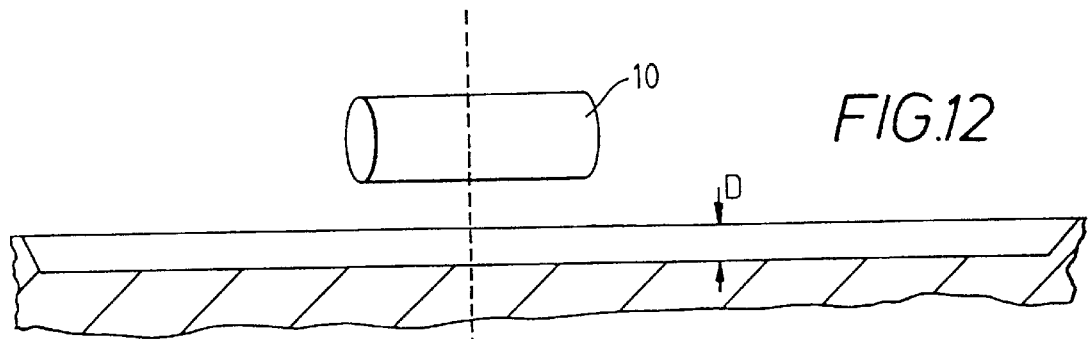
FIG. 12 corresponds to FIG. 10a, and shows the probe of FIG. 6 overlying a crack within a plate.
Figure 13A:
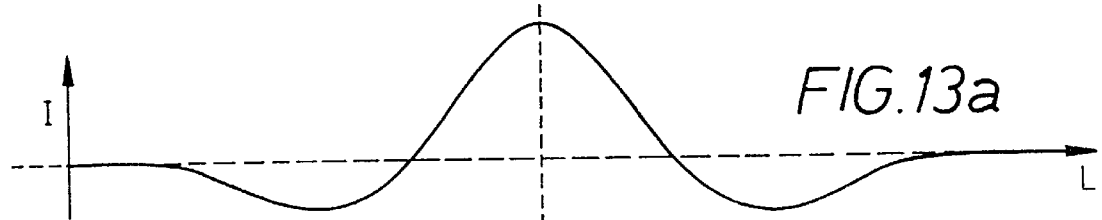
FIG. 13a shows schematically the current flowing across the crack along its length beneath the probe.

Referring to FIG. 12, a view corresponding to FIG. 10 is shown in which the conductive plate (shown in section) includes a relatively long crack of a depth D. As the depth D (as shown) is substantially constant, the resistance of the path down one side of the crack and up the other as shown in FIG. 1b is substantially constant. However, referring to FIG. 11, the current traversing the crack varies in magnitude and direction along the length of the crack, falling to zero well away from the excitation coil 10. The voltage drop across the sides of the crack therefore also varies along its length, according to Ohms law, as shown in FIG. 13a.

The graduated voltage along the crack will cause local minor current circulations, which are thereby dependent upon the local depth of the crack and the local rate of graduation of the surface currents as shown in FIG. 10b.

Figure 13B:
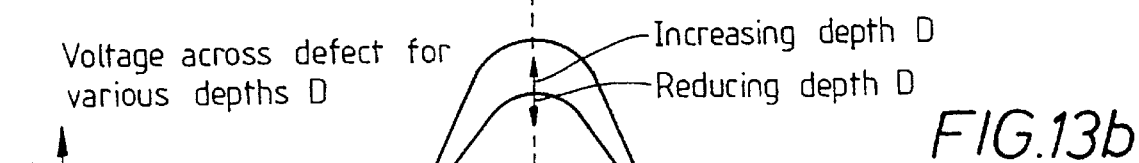
FIG. 13b shows the corresponding voltage drop across the crack, for varying crack depth.
Figure 13C:
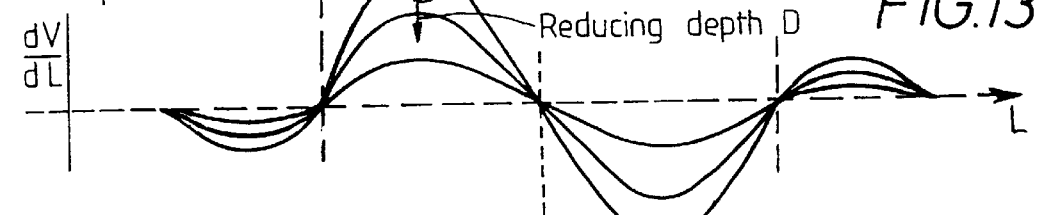
FIG. 13c shows the gradient of the voltage drop of FIG. 13b along the length of the crack, for varying crack depth.

As shown in FIG. 13b, the effect of the crack depth D is to vary the resistance in traversing the crack and consequently to increase the difference between highest and lowest values of potential difference across the crack (or, more generally, to vary the voltage gradient along the crack, as shown in FIG. 13c).

Referring further to FIG. 13c, it will be noted that the voltage gradient along the crack is zero at the position underlying the centre of the excitation coil 10, and anti-symmetrical about that position. It will thus be seen that, for this reason, the symmetrically postioned coils 20a–20c of the prior art shown in FIG. 3 will not under these circumstances generate an output signal since the positive and negative voltage gradients give rise to eddy currents which would, separately, induce a signal within the coils 20a–20c but together induce signals which exactly cancel.

The situation described above is modified when an end of the crack lies close to, or under, the coil 10 since beyond the end of the crack the potential difference is zero. The presence of the end of the crack close to the excitation coil 10 truncates one of the lobes of the voltage gradient plot shown in FIG. 13c, and consequently produces an asymmetrical gradient underneath the sensor coil 20, which correspondingly generates a signal. The magnitude of the signal will be largest when the end of the crack underlies the centre of the excitation coil 10. This behaviour corresponds to the signal shown in FIG. 5b. Some contribution to the signal may also arise from the tendency of current at the end of the crack to flow around the end, rather than beneath the end; so as to perturb the current flow.

Referring back to FIG. 6, if, as in embodiments of the invention, a coil 40 is positioned so as not to be symmetrically disposed about the centre of the coil 10. If no crack is present, a constant level of eddy current induces a predetermined constant coil output signal. In the situation shown in FIG. 12, where a crack underlies the whole length of the excitation coil 10 and beyond, there will be a net voltage gradient along the surface beneath the sensor coil 40 and a corresponding local flow of current about the crack, and consequently in the presence of the crack a signal of a magnitude corresponding to the crack depth will be generated. If the coil is positioned so that the greater part lies within the ends of the excitation coil 10, a signal of the form shown in FIG. 7b with peaks at the ends of the crack is obtained; otherwise, with an equal or greater part lying outside the coil 10, the peaks substantially disappear and a form like that shown in FIG. 5a or FIG.; 5b is obtained.

It is thus seen that the positioning of the coil or coils 40 relative to the magnetic fields generated by the excitation coil 10 is of considerable importance in determining the signal obtained. For deriving a signal which provides a strong indication of the crack depth, preferably the coil 40 is mounted so as to be positioned at a point of steep change of the inducing fields as this is the point at which the most significant crack depth related currents flow along the sides of the crack and are thus most easily measured. By inspection of FIG. 13c, it will be seen that the maxima of field change and of induced voltage lie at the ends of the excitation coil 10. In preferred embodiments, therefore, the coil 40 is positioned to have a substantial portion of its area at these positions.

FIG. 6 shows a single coil 40 positioned asymmetrically within the field generated by the excitation coil 10. As discussed in greater detail below, it would equally be possible to provide a second coil 40 at the other end of the excitation coil 10. If the two are connected directly together, the result is equivalent to the use of a single symmetrical coil as in the prior art. However, if the two are connected together differentially or in opposition the magnitudes of the induced signals are additive thus providing a larger output signal. As discussed below, this principle may be extended to provide a coil wound as a figure of "8", In other words in two contra-rotating lobes, centred at the middle of the excitation coil 10; in this case, the signals induced in the two lobes of the coil do not cancel, as in the coils 20 of the prior art, but are additive.

DESCRIPTION OF PARTICULAR EMBODIMENTS

First Embodiment

Figure 14:
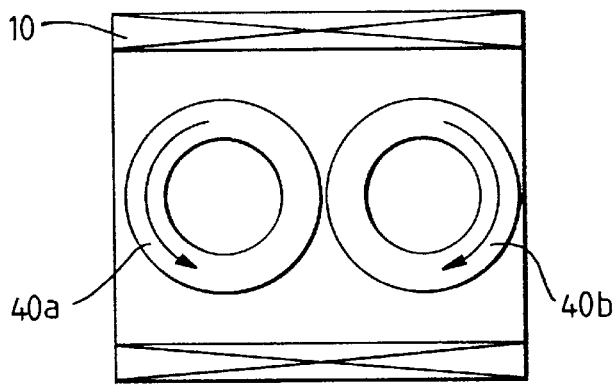
FIG. 14 shows the general arrangement of a first embodiment of the invention.
Figure 15A:
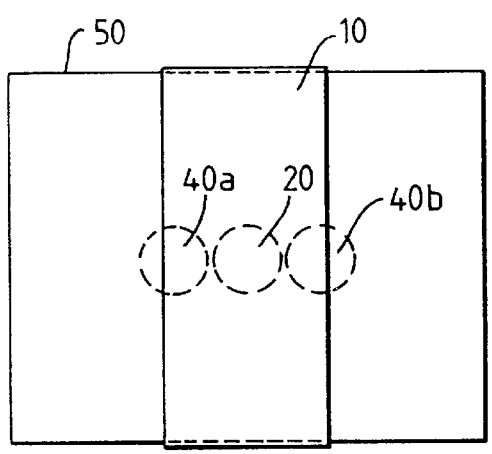
FIGS. 15a and 15b are respectively front and end elevations showing this embodiment in more detail.
Figure 15B:
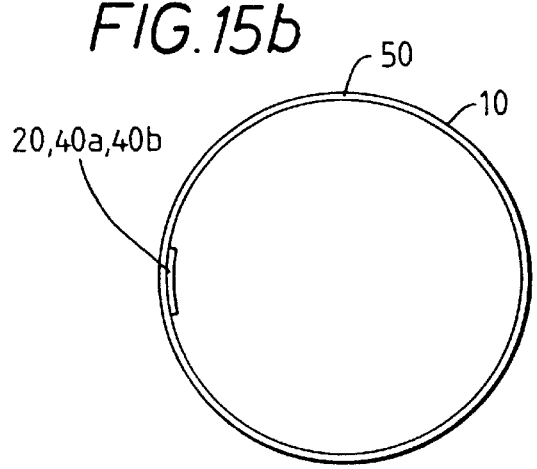
Figure 15C:
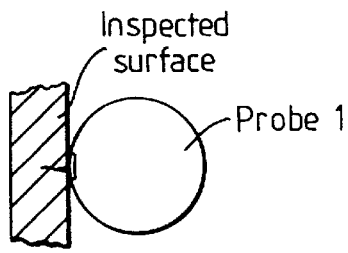
FIG. 15c shows the application of this embodiment in use.

Referring to FIG. 14, as mentioned above, the structure of FIG. 6 may be improved by the provision of a pair of coils 40a, 40b disposed symmetrically about the centre of the long axis of the excitation coil 10, but mutually connected In opposition so as to be wound in opposite senses. The exact longitudinal positions of the coils 40a, 40b are selected, as taught above, to achieve the desired response. Referring to FIG. 15a, the probe may comprise a cylindrical plastic tube former of external diameter 33 mm and internal diameter 31 mm, by providing thereon an excitation coil 10 comprising 60 turns of 0.2 mm diameter enamelled copper wire. A pair of coils connected in opposite senses 40a,40b each generally circular and comprising 50 turns of 0.05 mm diameter enamelled copper wire are provided, as shown, partially outside the edge of the excitation coil 10. A third coil 20 is provided centrally along the length of the excitation coil 10; for convenience, this coil is of the same dimensions and material as coils 40a,40b. As shown in FIG. 15b, the three coils 20, 40a,40b are adhered to the inner surface of the former 50. In use, as shown in FIG. 15c, the probe 1 is held against the surface to be inspected with the sensor coils 20, 40a, 40b adjacent to the surface.

The output of the coils 40a,40b in this embodiment is an AC output signal of a magnitude and phase angle corresponding to the crack depth and lift-off. Preferably, the signal corresponding to the difference between the coil outputs is processed to effect a complex plane rotation, so as to generate independent lift-off and crack depth signals, similarly to the "absolute coil" of the prior art as discussed above. The coil 20 provides a generally null signal with peaks when either end of the crack is passed, as with the current perturbation coil 20 of the prior art. This probe may thus, if desired, be used with an analyser 5 programmed to process the signals known from GB 2225115.

Figure 16:
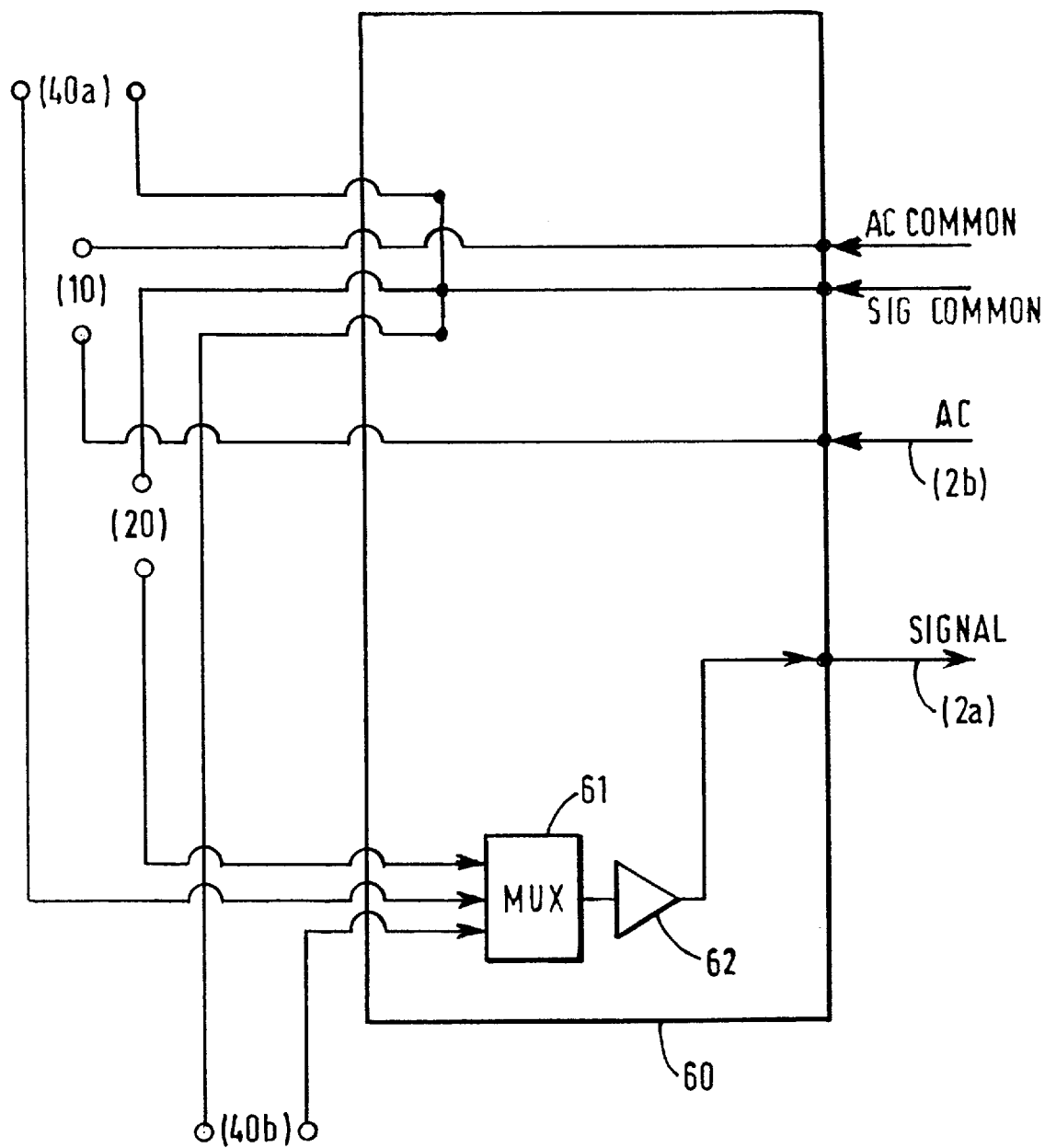
FIG. 16 shows schematically a driving circuit for connection to this embodiment.

Referring to FIG. 16, also included in the probe in this embodiment is a probe driving circuit 60 comprising terminals for receiving the cable 2 and for connecting one lead from each coil 10, 20, 40a, 40b to a common line thereof, and for connecting the AC power line 2b to the other side of the excitation coil 10. A suitable AC signal, for example a sinusoidal 250 mA peak-to-peak signal of a frequency sufficiently high to induce shallow eddy currents, is provided. The other ends of the sensors coil 20, 40a, 40b are connected to three inputs of a multiplexer chip 61 the output of which is connected to the signal line 2a. The power control lines for the multiplexer chip 61 may likewise be provided within the cable 2. The multiplexer 61 comprises any convenient analogue multiplexer device and is thereby arranged to alternately connect the output of each coil In turn to the signal line 2a for a predetermined period in accordance with a selection signal which may be supplied from the analyser 5. A line driver 62 may be provided to amplify the probe output signal for transmission over a long cable 2.

The probe assembly, including the former 50, coils and circuit 60, are encapsulated in a suitable hermetic seal by, for example, the application of a ceramic loaded epoxy resin, so as to be resistant to hostile environments such as seawater, or whatever the intended application of the probe is to be. The end of the cable 2 is preferably included In the encapsulation.

Although only three coils are shown, in practice a plurality of further sets of three coils could be provided distributed radially in a ring so that the probe can be applied in any orientation to the surface to be inspected; in this case, the multiplexer 61 includes an appropriate number of input channels. Where, as here, the two outputs of coils 40a and 40b are separately supplied the analyser 5 subtracts the outputs of the two prior to processing.

Second Embodiment

Figure 17:
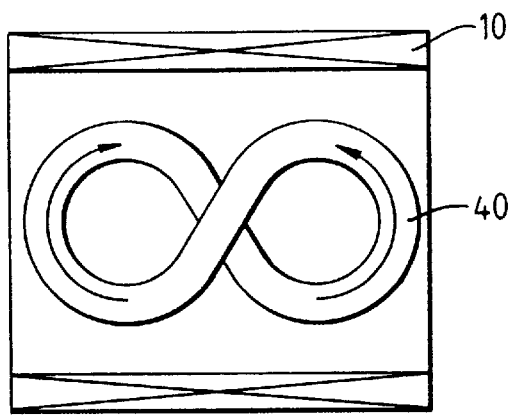
FIG. 17 shows schematically the general arrangement of a second embodiment of the invention.

Referring to FIG. 17, a second embodiment of the invention is illustrated in which corresponding parts are given corresponding reference numerals. In this embodiment, rather than using a single sensor coil asymmetrically disposed (as in FIG. 6) or a pair of symmetrically disposed but anti-symmetrically wound coils as in FIG. 14, a single coil 40 wound as figure of "8" centred on the longitudinal centre of the excitation coil 10 is provided. As shown, in this configuration, the effect of a given current is to Induce currents flowing in opposite directions at opposite ends of the coil, and the effects of exciting the two lobes of the coil from currents of equal magnitude but in opposite senses is therefore to produce additive currents in the coil.

Figure 18A:
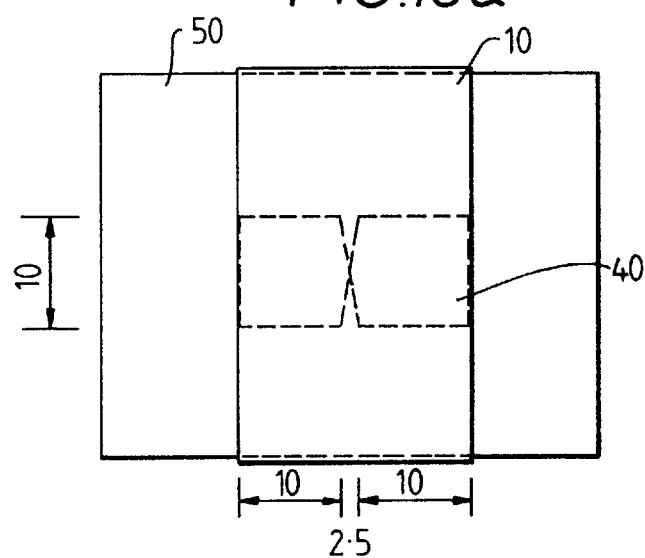
FIGS. 18a and 18b are front and end elevations respectively showing this embodiment In greater detail.
Figure 18B:
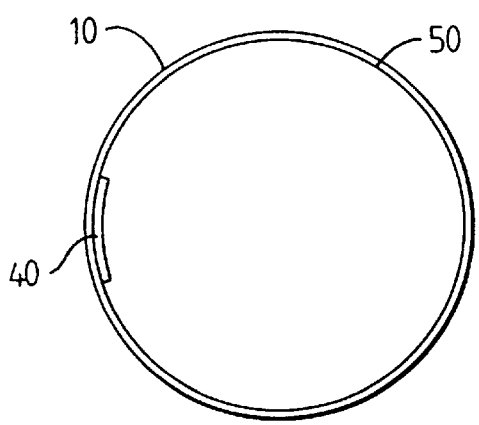

Referring to FIG. 18a, in which dimensions are shown in millimeters, in this embodiment the excitation coil 10 comprises 90 turns of 0.2 mm diameter enamelled copper wire and the figure of "8" wound coil 40 comprises 50 turns of 0.05 mm diameter enamelled copper wires; the dimensions of the former 50 may be as in the first embodiment and the sensor coil 40 comprises, as shown, two subtantially rectangular lobes adhered to the inner surface of the former end 50.

If, as shown only a single coil 40 is provided there is of course no need for the multiplexer 61, but as discussed in the first embodiment, a plurality of further coils 40 may be provided distributed radially around the probe in a ring so that the probe may be presented to a work surface in any orientation; in this case, the multiplexer 61 includes an appropriate number of inputs.

Returning now to FIG. 30c, by comparison with FIG. 30b, it will be seen that the output signal derived from a probe according to this embodiment is substantially closer to the idealised signal shown in FIG. 31a than is the output of the absolute coil of the prior art. Firstly, the line AC is both more linear and more vertical over a substantial portion of its length. Secondly, the line AB is both more linear and more horizontal, and shows a greater range in response to crack depths; it is also more normal to the lift-off locus so that greater separation between the effects of crack depth and lift-off can be achieved. Thus, in this embodiment the accuracy of the probe output is increased since it depends less upon a separation from the surface of the material being tested, and its range is likewise increased.

FIGS. 19a and 19b show, respectively, a sectional end elevation, and a semi cut-away front elevation corresponding thereto. Referring to the figures, a probe of the general type provided in the second embodiment comprises a central solid former 50 of, for example, nylon, symmetrically radially disposed in a ring around which are four rectangular current perturbation coils 20a–20d each provided as 50 turns of 0.05 mm enamelled copper wire, overlying which are provided four corresponding figure of "8" wound coils 40a–40d each provided as 50 turns of 0.05 mm diameter enamelled copper wire. Surrounding and partially overlying the figure of "8" wound coils 40a–40d is a ring shaped excitation coil 10 comprising 100 turns of 0.125 mm diameter enamelled copper wire; it will be seen from FIG. 19b that the disposition of the figure of "8" coils 40a–40d relative to that of the excitation coil 10 is such that the excitation coil 10 overlaps approximately half the area of each lobe of the figure of "8". A layer of sealing compound 70 (for example, ceramic loaded epoxy resin) surrounds the probe.

One example of a probe according to this embodiment was constructed to an overall diameter of 11.0 mm for use in a tube of 11.659 mm diameter, for the detection of defects or changes in internal diameter. The former 50 extends beyond the coils, as shown, in either direction, for mechanical attachment to cables, for example. Whilst the dimensions of the embodiments shown in FIGS. 19a and 19b may be scaled to suit other tube diameters, or other applications in general, it is noted that the ability of the probe to detect small defects is affected by the size of the sensor coils 40a–40d, 20a–20d and thus if the probe is significantly scaled up it is preferable to provide a large number of small sensor coils distributed radially around the probe rather than scaling up the dimensions of the illustrated sensor coils.

Where the probe diameter is small, the driver circuit of FIG. 16 is conveniently located distant from the probe.

Figure 20:
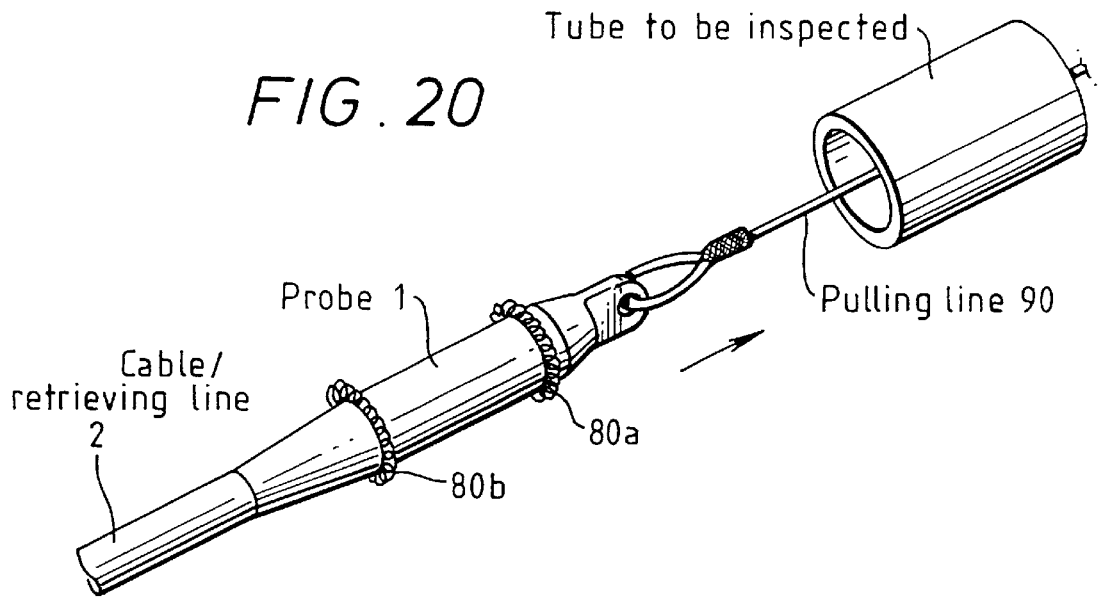
FIG. 20 shows one application of the embodiment of FIG. 19.

Referring to FIG. 20, in one particular embodiment, the probe of FIG. 19 (or of FIGS. 15–18) is particularly adapted for internal inspection of pipes by providing radially distributed leaf springs, coil springs or other resilient means 80a, 80b to space the probe from the walls of the tube and maintain it approximately centrally within the tube. Attached to the probe is a cable 2. Attached to the other end of the probe via fitting thereon is a line 90 for pulling the probe along the pipe. If the cable 2 is made sufficiently strong, the probe may be pulled back through the pipe by the cable so as to retrieve the probe. The cable 1 may be made rigid, or a flexible but incompressable rod so that the probe 1 may be pushed through the tube by the cable, without the need for a separate line 90.

In this embodiment, since the probe is maintained approximately centrally by the resilient means 80a, 80b and a plurality of radial lift-off signals can be derived from the coils 20a–20d, the profile of the pipe can be continuously measured in four directions. Changes in lift-off will indicate either a change in the pipe geometry (caused, for example, by a dent) or the thickness of a corrosion or other layer within the pipe between the mechanical surface of the pipe and an electrically conductive layer therebeneath. The lift-off measurements therefore, in this embodiment, provide valuable information about defects in the pipe as well as enabling the correction of crack detection measurements from the coils 40a–40d.

Figure 21:
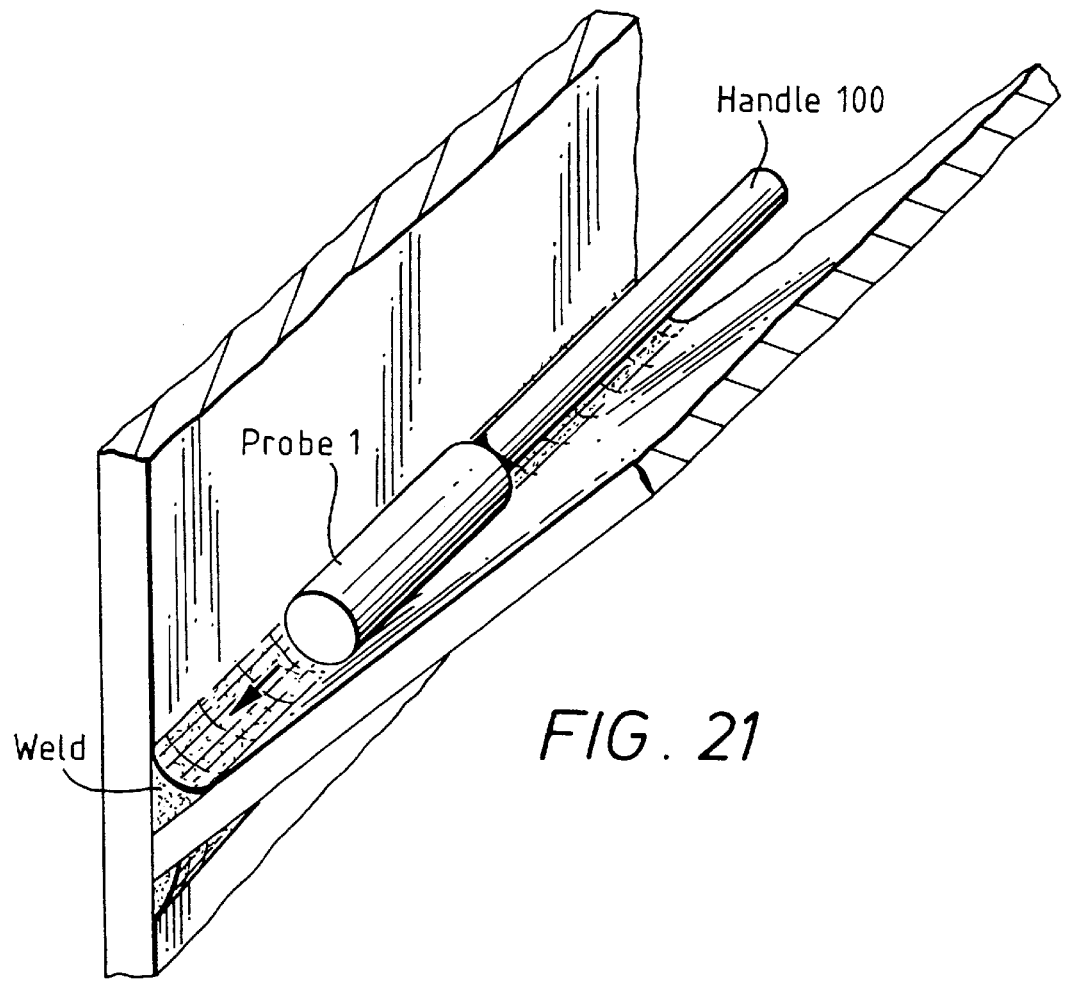
FIG. 21 shows schematically a second application of the embodiment of FIG. 19.

Referring to FIG. 21, the use of the probe of FIG. 19 (or FIGS. 15–18) in Inspecting an acute angled weld between two members is illustrated. The probe 1 has provided at one end thereof a rigid handle 100 with the aid of which the probe is pushed down the angle of the weld. The radius of the probe in this embodiment is therefore selected to match the expected radius of the weld. The cable 2 passes through the handle 110.

Third Embodiment

From the foregoing, it will be clear that the nature of the signal generated by the coil 40 in response to a crack or other surface defect will depend upon its position and geometry relative to those of the magnetic field generated by the excitation coil 10. For example, it has been shown that an elongate coil 20 disposed symmetrically along the length of the excitation coil 10 gives rise to a signal exhibiting peaks at detected ends of a crack but having zero amplitude along its length, whereas a coil positioned predominantly outside the solenoid 10 gives rise to a signal having a predetermined level when positioned over a crack, with no peaks.

In this embodiment of the invention, means are provided for electrically switching between different probe geometries, so as to vary the signal output by the coil 40 and thus obtain different types of signal sensitivity from the same coil, possibly by varying the sensor coil geometry but preferably by varying the magnetic field geometry. This could be done by providing two sensor coils 40 and switching the manner in which they are connected between direct and reversed or by processing the signals additively or subtractively, but in the embodiment shown in FIGS. 22a and 22b, a single sensor coil 40 is provided, located so as to partially overlap a pair of excitation coils 10a, 10b mounted end to end. A pair of switches 110a, 110b, ganged together, enable the AC supply to be routed either via one coil (10b) only or via both coils in series.

Referring to FIGS. 23a and 23b, the outputs of the coil 40 when the ganged switches 110a, 110b are in each position are shown in response to movement of the probe over a defect. When, as in FIG. 22a, the two excitation coils 10a, 10b are connected in series and effectively function as a single coil, the response to the defect shown in FIG. 23a is of the prior art form shown in FIG. 5b, whereas when only one coil is connected (10b), as in FIG. 22b, the response is according to the invention, a constant response with no substantial peaks over the length of the crack.

The probe system according to this embodiment to the invention therefore further comprises means for controlling the switch means 110a, 110b to alternate between the positions, and the analyser 5 is arranged to read the signal cable 2a in synchronism with the switching of excitation coils 10a,10b so as to separate signals generated by the coil 40 and separately log or plot those obtained for each excitation mode over time. Since the dimensions of the excitation coil 10 vary depending upon the position of the switches 110a, 110b, some different processing of the signals derived from the signal line 2a at respective times may be provided.

Rather than providing a single lobe coil, a figure of "8" coil could be provided.

The arrangement illustrated in FIG. 22 may naturally be extended to encompass large numbers of segments; for example, tests were carried out on an embodiment of the invention comprising four adjacent excitation coil segments wound on a plastic cylindrical former tube of approximately 33 mm external dimension, 31 mm internal dimension, each segment being 20 turns of wire occupying 5 mm along the former, to provide an overall excitation coil length of 20 mm. Two sensing coils are provided within the cylindrical former, each being wound with 50 turns of 0.05 mm enamelled copper wire, with dimensions approximately 9 mm×19 mm, parallel to the surface to be measured; one coil being a rectangular coil and the other a figure of "8" coil with equal lobes. Both sensors are positioned longitudinally symmetrically within the excitation coil.

The rectangular coil was found to behave as a prior art current perturbation sensor responding to the ends of defects when all four segments of the excitation coil were energised, and when only the outer two segments were energised, and to behave similarly with a reduced amplitude when only the inner two were energised. The figure of "8" coil is found to give "absolute" type measure of crack depth when all four segments were energised and when the inner two segments were energised, with much reduced amplitude when only the outer two segments were energised.

When only one end of segment was energised, the rectangular coil gives a signal responsive to the crack depth and the figure of 8 coil gives a response intermediate between an "absolute" type response and a "perturbation" type response. When two adjacent segments defining half of the excitation coil are energised, both coils give an intermediate response of this type.

Thus, a variety of different sensitivities to a defect can be produced from a single coil, depending on coil geometry, and its positional relationship to the magnetic field generated by the excitation generator. The number of output lines required from different sensors can therefore be reduced, and one type of coil geometry (for example, flat coils coplanar with the surface to be measured) can be used to generate several different types of measurement leading to a simplification and manufacturing.

Fourth Embodiment

In the previously described embodiments, the probe is mechanically moved over a surface typically by an operator and consequently measurements of the distance or crack length along the surface are derived on the assumption of constant probe speed of motion. This assumption is optimistic, however, where a human operator is working under difficult conditions (such as a diver inspecting a submerged structure) and so the accuracy of crack positioning and length measurements cannot be guaranteed. Furthermore, moving the probe at a constant and steady speed is laborious and Lime-consuming for the operator and calls for skill and patience under, sometimes, difficult working conditions.

Accordingly, in this embodiment of the invention, a plurality of separate sensors are provided in a one or two dimensional array which is laid over an area of a surface to be surveyed for cracks, and means are provided for reading the sensors so as to automatically measure the response along the line or across an area directly, without the need for moving the apparatus. Distance measurements are thus derived directly in terms of distance, rather than from measurements taken over time and converted to distance on an assumption of constant speed.

One particular example is shown in FIG. 24, in which the excitation coil 10 is tapped in the manner shown in FIG. 22 at a plurality of points along Its length so as to be divided into a plurality of separately energisable segments. Associated with each segment is a coil 40*a*–40*e* provided so as to lie asymmetrically within the magnetic field generated by the respective segment; the coils may also be arranged, as shown in FIG. 22, so as to be symmetrically disposed between a pair of adjacent segments when energised together. A control unit 120 is connected to control the energisation of the segments. In one embodiment, the control unit 120 is arranged to energise each segment in turn, or each alternate segment, and route the signal from the associated coil 40*a* to the signal line 2*a*. This is advantageous in that when only one coil is energized at a time, the magnetic fields from different coils of the array cannot affect the current sensed by each sensor coil 40*a*–40*e*. However, segments of the excitation coil 10 may be excited together provided they are sufficiently widely separated; for example, every fourth coil may be energised together.

If only one coil at a time is energised, then the resulting signal derived from the signal line 2*a* corresponds to a stepwise approximation to the signal derived in the above described embodiments where the coil itself is moved; this embodiment corresponds to moving the point of application of the magnetic field rather than moving the probe itself.

Preferably, the control device 120 is arranged to operate also in the mode shown in FIG. 22, so that either a single segment or a pair of segments can be energised at a given time, so as to be able to derive separate output signals corresponding to crack depth and to the occurrence of the ends of the crack as described above, by causing the energised sections of the coil 10 to either overlap symmetrically or overlap asymmetrically with the current perturbation coils 40*a*–40*e*.

This arrangement may further be extended to replace the tapped excitation coil 10 of FIG. 24 by a plurality of discrete excitation sources each associated with one of the sensing coils 40*a*–40*e*. For example, the discrete excitation sources may be ferrite beads aligned in a two-dimensional array and each energised by an appropriate energising winding, as in computer core storage arrangements. The array may be made two dimensional to scan an entire surface without mechanical motion. Preferably, in this embodiment, the array is formed on a flexible substrate so as to be capable of conforming closely to a surface of varying sizes. The same is, naturally, true of the embodiment of FIG. 24; by providing the former on which the windings of the excitation coil 10 are provided as a flexible rod, the array may be fitted to varying workplace geometries.

Referring to FIG. 25, in which dimensions are shown in millimeters, in another particular embodiment if this form of the invention, a central generally rectangular former 50 shown in FIGS. 25*a* and 25*b* has provided thereupon four spaced apart excitation windings 10*a*–10*d* (similar materials to the above described examples may be employed) within each of which is provided, on one face, an oval centrally positioned flat coil 20 providing a signal, as discussed above, indicating the detection of the end of the crack, and a figure of "8" wound coil 40 (provided outwardly of the coil 20) having generally rectangular lobes as shown in FIG. 26. The excitation coils 10*a*–10*d* are spaced apart so that their magnetic fields do not significantly overlap.

As described above, the coils may be energised sequentially in a scan or a plurality may be energized together; in the former case, the sensors 40*a*–40*d* and 20*a*–20*d* may be connected in common to a single signalling line 2*a*, whereas in the latter case their outputs may be multiplexed as described above onto a single line.

Figure 31:
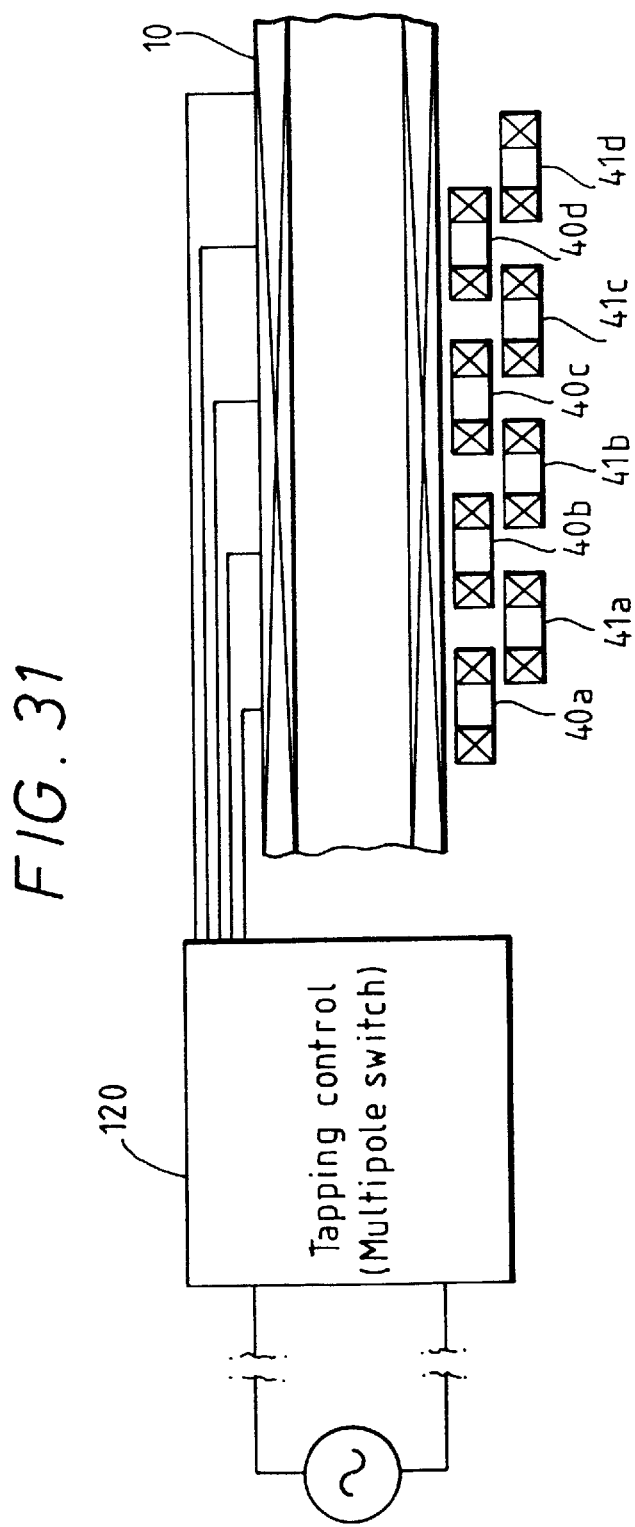
FIG. 31 shows a schematic sectional elevation of an alternative embodiment to that of FIG. 24.

Referring to FIG. 31, in an alternative arrangement according to this embodiment of the invention, the arrangement of FIG. 24 is modified by the inclusion of a further set of coils 41*a*–41*d*, equivalent to the coils 40*a*–40*d* but offset relative thereto along the axis of the solenoid 10. Thus, at each segment of the solenoid 10, two coils 40, 41 are provided in the field generated thereby, at different positions along the field. It will be clear from the foregoing that the two coils 40, 41 will therefore exhibit different sensitivities to the presence of a flaw.

As shown in FIG. 31, the second set of coils 41*a*–41*d* are staggered, in one example, relative to the first set 40 so as to have their maximum sensitivity to cracks at positions where the first set have their minimum sensitivity to cracks. For example, one set of coils may be positioned symmetrically within each segment of the excitation solenoid 10, and the other set overlying the joins between the excitation coil segments. Thus, if the single segments of the solenoid 10 are energised, one set of coils provide a curent perturbation signal indicating the ends of defects, and the other set provide an absolute current signal indicating the depth of defects present within the field of the energised solenoid segment. If two adjacent solenoid segments are energised, of course, the response of the coils is reversed.

Thus, in arrangement according to FIG. 31, each coil 40a–40d of the first set of coils can provide a crack depth measurement when one of the two segments of the excitation solenoid adjacent to coil is energised, or can provide (when its output is suitably scaled) a sensitive indication of the presence of a crack end when both the excitation solenoid segments adjacent to it are energised. Likewise, each coil 41a–41d of the second set of coils can provide an indication of the presence of a crack end when the solenoid segment with which it is aligned is energised, or an indication of a crack depth at a position intermediate between two neighbouring coils of the first set 40 when a pair of adjacent solenoid segments are energised; in this cases conveniently, the outputs of the coil of the second set and of its neighbour adjacent to the next energised solenoid are processed subtractively or connected back-to-back by a switch, so as to provide a figure of "8" type response discussed above.

Thus, the second set of coils provides crack depth, crack presence or liftoff related signals from points in between those points given by the outputs of the first set of coils. Still further sets of coils, positioned staggered relative to the first and second sets, could be provided to further increase the resolution of the probe. In sensors according to this embodiment, the position or resolution of the sensor is dependent upon the increment of the excitation field position, which is finer than the pitch of the individual sensor coils; the increment of movement of the excitation field may be smaller than the length of each segment of the excitation solenoid 10 where the control unit 120 is arranged to be capable of energising adjacent segments together as well as individually.

In an example of an arrangement according to FIG. 31, the excitation coil 10 is 50 mm long and comprises 80 turns, tapped every four turns to provide 21 connections dividing the excitation coil 10 into 20 separately energisable segments. The excitation coil 10 conveniently uses 80 way 0.635 mm pitch ribbon cable, connected with ends offset, suitably tapped. The tapping control 120 comprises set of digitally controlled relays selecting one or more of a segments; for example, operating under control of a microprocessor. The material of the sensor coils may be as above.

Referring to FIG. 32a, rather than providing two sets of coils 40a–40d, 41a–41d, each with a pair of discrete ends, each set of coils 40, 41 may be substituted by a single elongate coil comprising a plurality of lobes at the pitch of the spacing between excitation coil segments. The same is, of course, true of the embodiment of FIG. 24.

As shown, each lobe is wound in the opposite direction to its neighbours, so that the two extended coils 40, 41 are staggered so that the centre of the lobes of one coil corresponds to the join between lobes of another, so that the sensitivity of one coil is maximum where that of the other is a minimum and vice versa as shown in FIG. 32b (which indicates the magnitude of the output of each coil to a defect position along the length of the coil).

Each of the coils 40, 41 may be made by forming a plurality of turns in a first direction and then a plurality of turns in a second direction spaced along from the first, and so on, or by winding a wire on a serpentine path forwardly and backwardly along the entire length of the sensor. Corresponding materials and number of turns to the previous examples may be used, but the preferred materials and number of coils are readily determined experimentally.

Referring to FIG. 33, in an alternative arrangement to that of FIG. 31, the two sensor coil assemblies 40, 41 are laid either just within or just outside the excitation coil 10 which may be the same as in FIG. 31, with the tap separation for example at 2.54 mm intervals. The centres of the fields produced by each tapped segment therefore lie at spacings of (n+0.5)* 2.54 mm Interval spacings from the ends of the coil. It is also possible to produce intervening field centres, as mentioned above, by energising several adjacent centres; for example with two adjacent segments excited, the magnetic field is centred above the middle tap of the two segments and consequently interspersed field centres at n* 2.54 mm from the ends of the coil can also be produced.

The centres of the lobes of the two elongate coils 40, 41 are arranged to correspond to the centres of the magnetic excitation field thus produced from the taps; one set (40) may have lobes centred at the join between adjacent segments, and the other set (41) may have centres coinciding with the centres of the excitation coil 10 segments.

If two segments of the excitation coil 10 are simultaneously energised, the magnetic field strength produced will be higher than if only a single segment is used. We have found that it can be treated as being twice as high, and therefore when 2 adjacent segments are energised the energising current may be halved or the signals derived from the coils 40, 41 may be halved to correct for this.

It will be recalled that each figure of "8" winding corresponds to 2 coils connected "back-to-back"; that is in opposite rotational senses so that their outputs are subtractive rather than additive. Accordingly, the effects of the extended figure of "8" coils 40, 41 can be achieved by providing separate coils as shown in FIG. 31, and either connecting them back-to-back or reading the signals from the coils and then performing a signal processing step of subtracting the coil outputs; thus, an array of separate coils can be processed by subtracting adjacent outputs to provide a corresponding signal.

It will be clear from the foregoing that the general principle of providing a travelling excitation field scanned electrically along a surface and employing eddy current sensing means along It is itself advantageous; particularly if the sensing means comprise two or more relatively offset sub arrays 40, 41. Although very preferably inductive coils are used as the sensing means, other eddy current sensing means could be used.

Referring to FIG. 40, in one construction a flexible sensor array is provided as a plurality of flat wound coils 40a–40e each mounted on a substrate 140a–140e, the substrates being connected at one point to an underlying substrate(not shown). As shown, each substrate 140 may be connected to an excitation coil winding, or windings, 10a–10e. Each of the coils 40a–40e may conveniently be fabricated on the substrates 140a–140e by printed circuit fabrication techniques for printing inductors. The excitation windings 10 are, for example, mounted on a flexible sheet substrate so that the probe can be brought Into contact with the surface, and the individual substrates 140a–140e can each flatten against the surface. The substrates 140a–140e need not be mounted to overlap, if lower resolution is acceptable.

Figure 37:
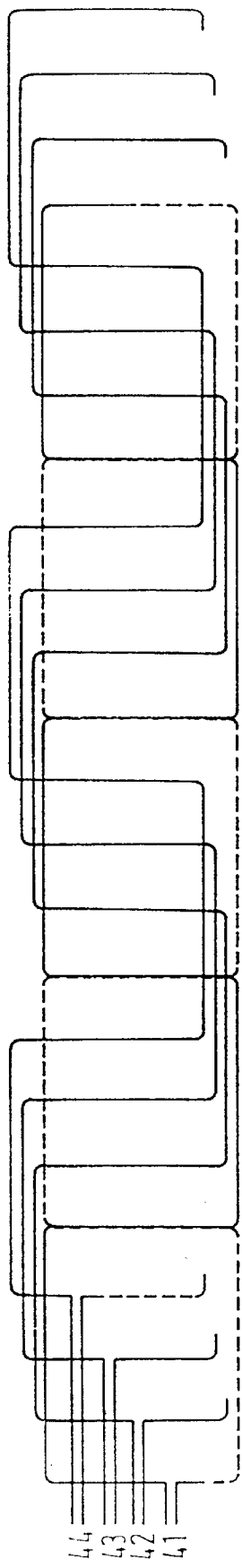

Referring to FIG. 37, in a further example, the probe indicated generally in FIGS. 32a and 33 is modified to provide four elongate sensors 41–44 each comprising a coil wound about a serpentine path to define a series of contra-rotating lobes 41a–41e etc; FIG. 37 shows the return path for one sensor as a dashed line and the others correspond. Each sensor 41–44 typically may comprise 10 turns of enamelled copper wire, formed by winding the wire about an elongate rectangular array of pins at the corners of each of the lobes. The four sensors 41–44 are staggered so that the intersection of the lobes of each are displaced, relative to its neighbours, by one quarter length of each lobe corresponding to one segment length. For clarity, the four sensors 41–44 are shown as laterally offset; in fact in use they are laterally aligned.

As indicated in FIG. 37, each intersection between a pair of lobes is positioned to lie at the centre of a separate excitation winding $10_1$-$10_{16}$, separately energised by the tap control circuit 120, typically in a sequence 10. The excitation windings 10 are omitted from FIG. 37 for clarity. The excitation windings are provided as a substantially flat coil 10 adjacent an elongate board on to which the sensors 41–44 are wound, the board, sensor coils 41–44 and excitation coil 10 subsequently being sealed in thermosetting resin.

Figure 38:
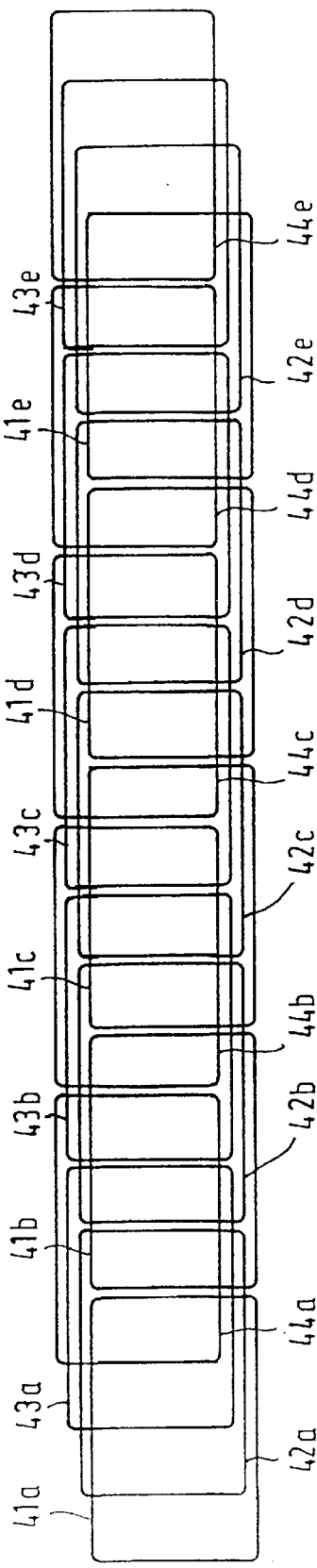
FIG. 38 shows schematically the arrangement of sensors in an alternative embodiment to that of FIG. 37.

Referring to FIG. 38, in an alternative construction corresponding to FIG. 31, 20 separate coils 41a–41e, 42a–42e, 43a–43e, 44a–44e are provided. Each coil corresponds In position and size to one of the lobes of the sensors 41–44 of FIG. 37; thus, the set of four coils 41a–41d lies at the same locations as the four lobes of the sensor 41 of FIG. 37, and so on.

If a similar number of turns and material are used, identical outputs can be derived from the sensors of FIG. 38 to those of the four sensors 41–44 of FIG. 37, if the coil outputs are connected as follows:

$$41 = 41a - 41b + 41c - 41d + 41e$$

$$42 = 42a - 42b + 42c - 42d + 42e$$

$$43 = 43a - 43b + 43c - 43d + 43e$$

$$44 = 44a - 44b + 44c - 44d + 44e$$

When any single excitation winding is energised the coils adjacent the winding will deliver substantial signals; It would therefore be possible to selectively form the signal required from only the coils corresponding to the winding energised. Flaw depth information is obtainable from the pair of coils meeting at the excitation winding, and end information from the coil centred at the winding.

Table 1 extends the above relationships, and shows normalisation coefficients for the summation of the outputs of the coils for each energised winding.

Table 2 correspondingly provides normalisation coefficients for the summation of the coil outputs to detect crack ends or other sources of current perturbation.

It will be evident that the coefficient tables can be extended to correspond to large numbers of overlaid sensor lines; the table repeat interval will be seen to correspond to twice the number of overlaid sensor lines. Different coefficients could be employed, for example to enhance the sensitivity at the cost of resolution or vice versa.

In the embodiment of FIG. 38, the coils 41a–e, for example, may therefore be connected to a single common output line, the two output wires of each coil 41a, 41c, 41e being connected in a first sense and those of the intervening coils 41b, 41d being connected in a second, reverse, sense. This provides a limited number of wires for a long array. However, it would be possible alternatively to provide a plurality of output wires, one for each coil, and allow the analyser 5 to combine the outputs as desired.

Fifth Embodiment

In another embodiment, a two dimensional scanning array probe may be provided by providing an array comprising several elongate one dimensional arrangements of the type shown in FIG. 24 or FIG. 31 or FIG. 33. By providing that the tapping control units 120 of each of the adjacent aligned excitation coils 10 is separately energisable, and by energising diagonally arranged segments of adjacent excitation coils, it will thus be possible to provide a probe in which the direction of sensitivity can be rotated, so as to respond to cracks lying at 45° to the axis of the excitation coils (or indeed at other angles). By varying the pattern of segments of adjacent excitation coils which are energised, different field directions and hence different directional responses, or omni directional responses, can be obtained.

By employing a plurality of elongate, aligned sensor arrangements each having only a single output line to provide a two dimensional sensor array, in which the sensed position along each sensing arrangement is varied by varying the excitation field position, the number of output lines (Or multiplex channels) is directly proportional to the linear dimension of the two dimensional array rather than to its area. If, by way of comparison, a two dimensional array of discrete sensors were provided instead then the number of sensor output lines or multiplex channels required would rise with the square of the linear dimension of the array. This embodiment of the invention therefore enables the construction of large area two dimensional sensing arrays for material surface measurements without requiring high speed or complex multiplexing arrangement, or a large number of different signal lines, between the probe and the logging or analysis system to which it is connected.

Figure 39A:
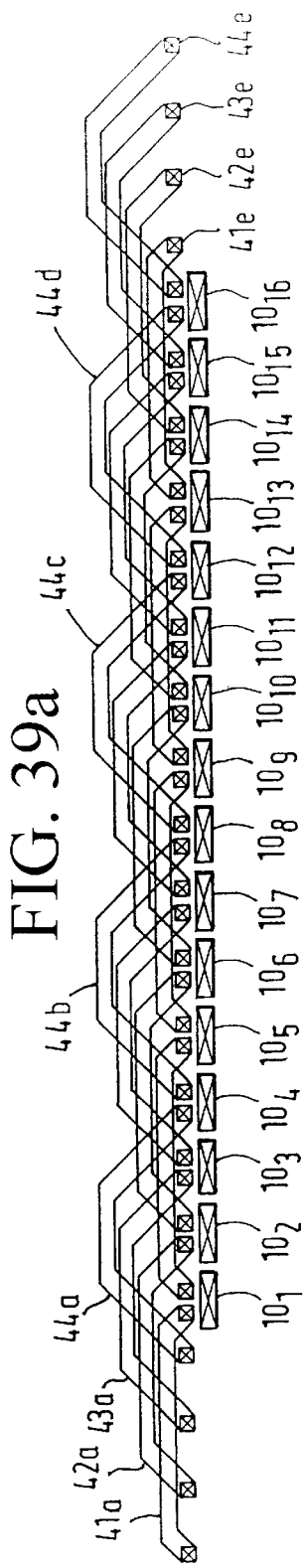
FIG. 39a is a sectional front elevation through a two dimensional scanning probe arrangement.
Figure 39B:
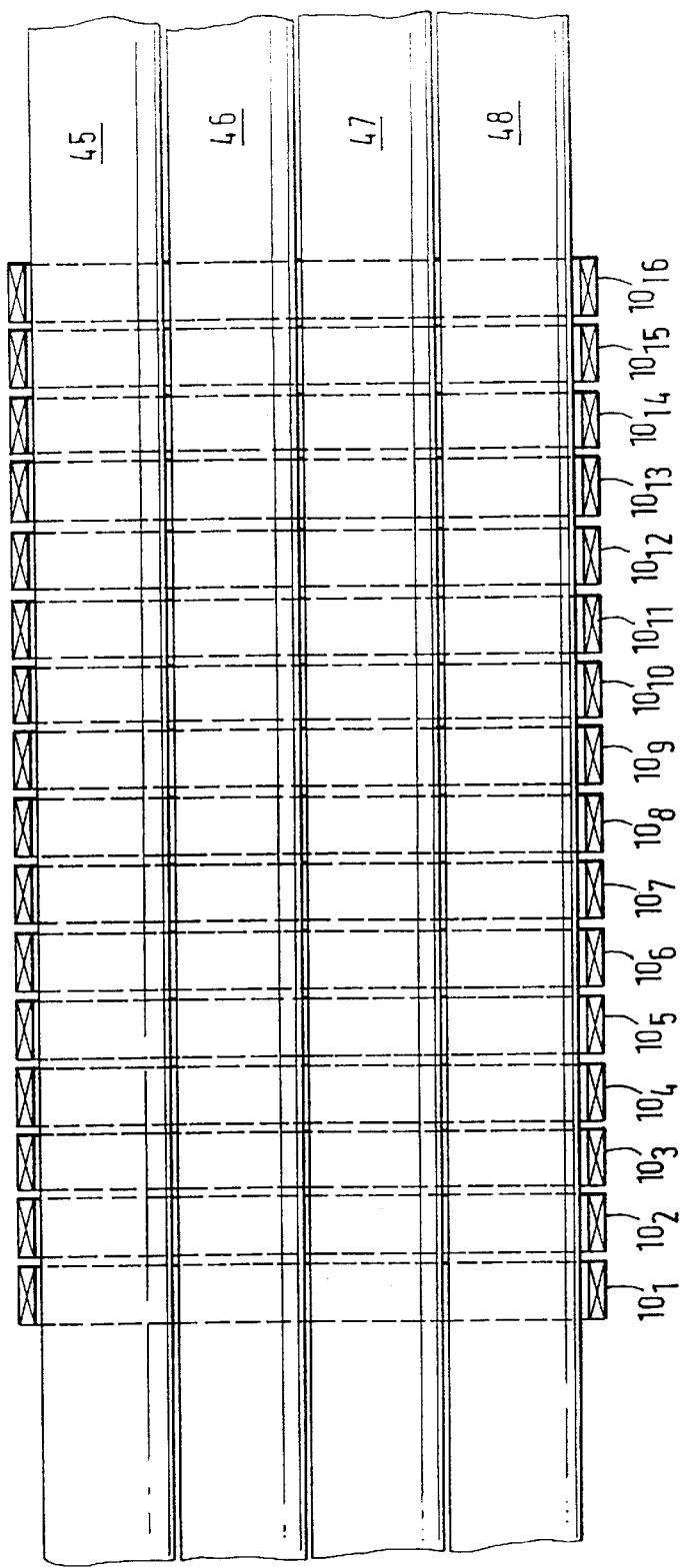

Referring to FIG. 39, as shown in FIG. 39b a two dimensional array probe comprises a plurality of linearly extending sensors 45–48, each corresponding to the sensor arrangement shown in FIG. 38. Each sensor 45–48 therefore has a single output line to run through the cable 2 to the analyser 5 (or to be multiplexed together).

Provided around the sensors 45–48 is a linear array of excitation windings $10_1$-$10_{16}$, each of which is separately connected to the tapping control 120 to be energised. The arrangement of the coils 41a–44e, 42a–42e etc within one of the sensors 45 is shown in FIG. 39a in section.

In the illustrated embodiment, each of the excitation windings is energised in turn, and a reading is taken from the four linear sensors 45–48. A two dimensional map of any defects aligned with the sensors 45–48 in the two dimensional area under the probe is thereby available from the readings taken. The sensor may be extended in the direction of the linear sensors 45–48 without any increase in the number of connection wires (although the time taken to scan the area will be slower), and thus increasing the area of the sensor in two dimensions causes only a linear increase in the number of connection wires required.

To obtain a mapping of defects which are inclined at other angles, a second layer of excitation windings and elongate sensors may be provided above or below that of FIG. 39 and lying at an angle (for example orthogonal) thereto. A second scan in a different direction can therefore be performed, and the results of the two scans combined to provide a two dimensional map of defects at varying inclinations to the sensors.

In a sensor useful for underwater structures, the structure described above with reference to FIG. 39 is adopted, extended to provide 40 coils within each of the sensors 45–48 and 39 excitation windings $10_1$-$10_{39}$. The tapping controller 120 comprises a multiplexing circuit selectively connecting each of the windings $10_1$-$10_{39}$ in turn to the AC power line 2b. The excitation windings 10, sensors 45–48 and control 120 are provided as a unit sealed in resin for use on underwater structures.

Three Dimensional Output Display

It is convenient to display the output of a probe according to the above embodiments as a three dimensional trace, in which two directions (X, Y) refer to the combination of excitation winding and sensor giving rise to the defect signal, and the third dimension (Z) represents the defect signal value (e.g. crack depth). Such a display is readily generated as, for example, a surface defined by contour lines connecting points having the same X value and points having the same Y value to provide a mesh which may be displayed or plotted in any convenient isometrical prospective convention, preferably with hidden lines removed. Likewise, where liftoff information is calculated from the probe outputs, this can correspondingly be represented.

Sixth Embodiment

Figure 27A:
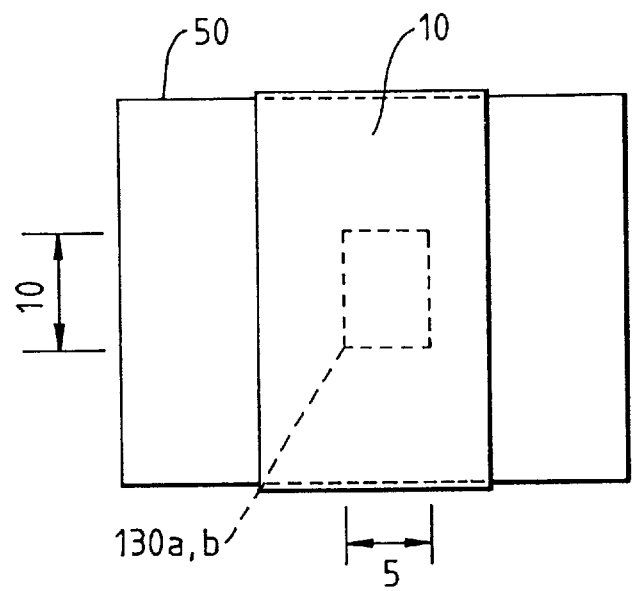
FIGS. 27a and 27b are respectively front and end elevations of a fifth embodiment of the invention.
Figure 27B:
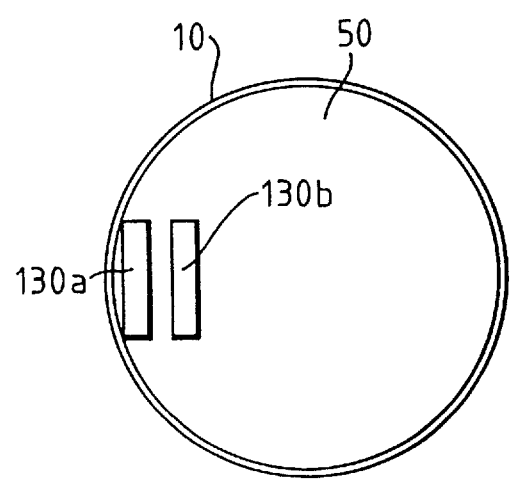

Referring to FIG. 27a and b, in an alternative arrangement, a former 50 of the type employed in the first embodiment may be used having wound thereupon an excitation coil 10 comprising 80 turns of 0.2 mm diameter enamelled copper wire. Within the former 50 is provided a flat vertical rectangular sensor coil 130a of height 2 mm having an axis parallel to the excitation coil axis, comprising 50 turns of 0.08 mm diameter enamelled copper wires and spaced axially therefrom (e.g. by 2 mm) is a second (or several) similar coaxial coil(s) (130b) so as to lie at a different height from the workpiece. The two coils are connected in opposition and are located centrally of the length of the excitation coil 10. The output of a single coil would therefore be of the prior art form shown in FIG. 5b. However, since the spacing between the first coil and the workplace differs from that between the second coil and the workpiece, the current signals are of different magnitudes in the two coils; connecting the coils in opposition (so that induced current flaws in opposite directions) thus gives rise to a net additive output signal which can be used to indicate crack depth. On the other hand, the background output (in the absence of a crack) from the two coils is subtractive. This embodiment thus makes use of the vertical field gradient above the crack. Other types of sensor coil may of course be present additionally.

Alternatives and Modifications

From the foregoing, it will be clear that the factor determining the type of signal derived from a sensor responsive to current perturbation in the surface is determined by the position of the sensor(s) in the (non-uniform) excitation field. Some further examples of sensor geometries will be briefly discussed with reference to FIGS. 28a–k and corresponding probe output signals (processed as discussed above responsive to detected cracks) are shown In FIGS. 29a–k for traversing a crack.

Figure 28A:
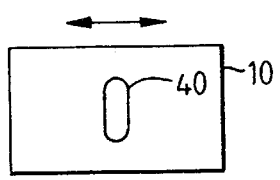
FIGS. 28a–i shows schematically various alternative geometries according to the invention and the prior art.
Figure 29A:
FIGS. 29a–k show corresponding output signals generated in response to traversing a crack.

Referring to FIG. 28a, the current perturbation sensing coil 40 is positioned centrally with respect to lengthwise axis of the excitation coil 10, but its axis is rotated through 90 degrees relative to that used in GB 2225115. As shown in FIG. 29a, the signal derived in traversing the crack is similar to that in FIG. 5a with a peak corresponding to either end of the crack and a null signal in between.

Figure 28B:
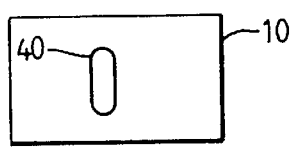
Figure 29B:
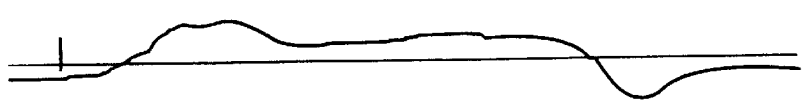

Referring to FIG. 28b, if the coil 40 is now slightly displaced from the centre position along the length of the excitation coil 40 as to lie asymmetrically in the magnetic field thereof, the output signal shown in FIG. 29b retains a peak corresponding to each end of the crack but has a non-zero magnitude along the length of the crack.

Figure 28C:
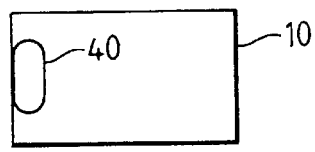
Figure 29C:
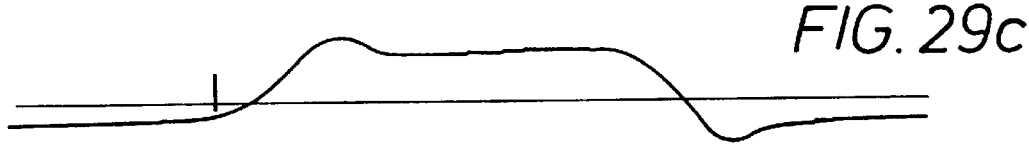

Referring to FIG. 28c, if the coil 40 is displaced to a position within the end of the excitation coil, the predominant feature of the output signal is substantially constant region along the length of the crack of a depth relating to the crack depth. Peaks corresponding to either end of the crack remain, however.

Figure 28D:
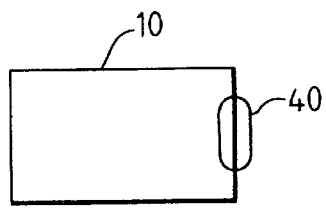
Figure 29D:
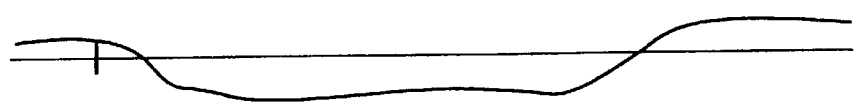

Referring to FIG. 28d, when the sensor coil 40 is positioned with its area equally distributed around the end of the excitation coil 10, the peaks substantially disappear as shown in FIG. 29d.

Figure 28E:
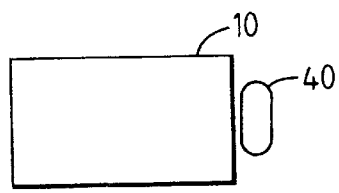
Figure 29E:

Referring to FIG. 28e, if the sensor coil 40 is positioned outside the excitation coil 10, but within its magnetic field, no peaks are present and the edges of the region of constant amplitude corresponding to the crack are of shallower inclination.

Figure 28F:
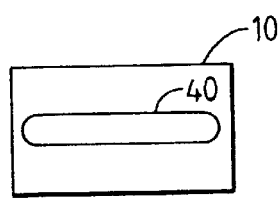
Figure 29F:

Referring to FIG. 28f, for reference, the sensor coil Is positioned to correspond to the alignment of the current perturbation coil in the prior art.

Figure 28G:
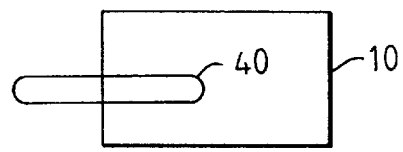

Referring to FIG. 28g, the geometry corresponds to that of FIG. 28d except that the long axis of the sensor coil 40 runs parallel to that of the excitation coil 10. The form of the signal of FIG. 29g is seen to be similar to that of FIG. 29d.

Figure 29G:
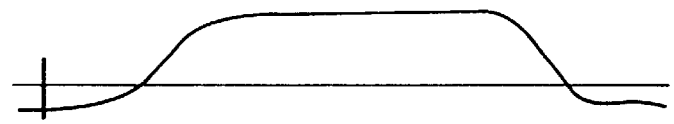
Figure 28H:
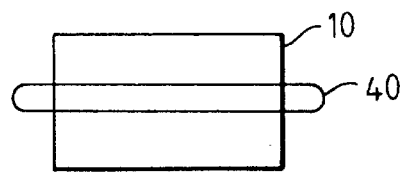
Figure 29H:

In FIG. 28h, the length of the sensor coil 40 of FIG. 28f is increased relative to that of the excitation coil 10 so as to extend beyond the ends of the coil in either direction; as shown in FIG. 29h this does not significantly alter the bipolar peaked nature of the output signal derived from the sensor.

Figure 28I:
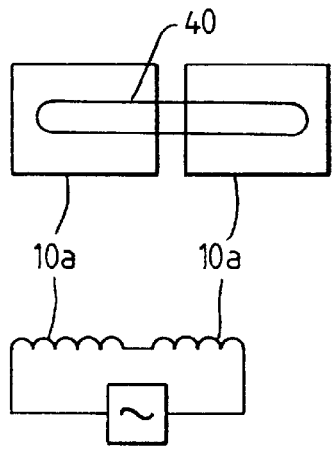

Referring to FIGS. 28i–28k, various connections of the geometry of the embodiment of FIG. 22 are shown. In FIG. 28i, the two coils, 10a,10b are connected in series, so that the sensor coil lies symmetrically within the joint magnetic field, so that the output signals of FIG. 29a corresponds to that of FIG. 28f.

Figure 29I:
Figure 29J:
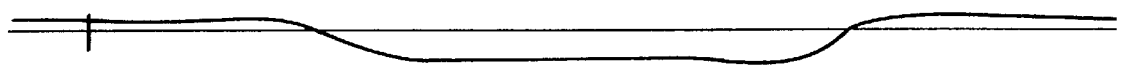

Referring to FIG. 28j, when one of the coils 10b is not energised the arrangement of the sensor coil 40 corresponds to that of FIG. 28g, so that the output signals shown in FIG. 29j resemble those of FIG. 29g.

Figure 29K:

Referring to FIG. 28k, if the two excitation coils 10a,10b are connected back-to-back the resulting output signal is shown in FIG. 29k, in which the peaks have disappeared; this would appear to correspond to the addition, in similar senses, of two waveforms of FIGS. 29j displaced in time.

To sum up, the shape of the sensor coil is found to be less significant than the symmetry of its position in the magnetic field. The long axis of the sensor coil may be oriented normal to the long axis of the solenoid coil 10. We have also found that a sensor coil inclined at a skew angle (e.g. 15°) to the solenoid coil axis provides an output signal according to the invention if a crack is traversed off the centre line of the solenoid since the perturbations caused by the crack in this case are asymmetrically seen by the sensor coil (the portion of which nearest the crack generates the higher output).

Many other modifications or alternative geometries may be adopted whilst maintaining the spirit and scope of the invention; for instance, different number of turns may be employed, or different wire materials may be employed, or different means for sensing perturbation currents or potential difference gradients may be provided (for example, suitably connected Hall effect sensors), or different sources of magnetic field may be provided. Furthermore, although the invention is particularly suitable for use in difficult or dangerous environment such as oil rigs and pipeline testing, it is equally suitable for use in detection of cracks in, for example, aircraft.

Preferably, means may be provided for energising the excitation coil 10 with AC currents of different frequencies. Each frequency may be selected to correspond to different material, or multiple frequencies may be used on a single surface to be measured; since different frequencies generate eddy currents penetrating to different depths, by using multiple different frequencies, a three dimensional scan of the defects below the surface can be produced penetrating to different depths. Multiple frequencies could also be employed to produce a mapping of distribution of different materials within a surface. The output signals produced by the surface measuring apparatus described in the above embodiments could be employed as the input data for, example, a finite elements modelling program, for calculating for example stress distributions within a structure to be tested.

It will be understood from the foregoing that the generally flat arrays shown in FIGS. 37–39 may be alternatively formed to conform to a cylindrical sector for the inspection of, for example, tubes or curved welds.

The array may likewise be conformed to more complex curves or geometries for the inspection of particular other components. In this case, sensor arrays may be produced by taking a casting from the component which it is desired to inspect, and then forming the sensor array using the casting.

Where such a conformal shaped sensor array is employed, it may be used not only to locate flaws or material changes but also, by measuring the liftoff from the component, dimensional tolerances and accuracy of formation of the component.

In the light of the foregoing, the invention is limited only by the scope of the accompanying claims as granted, and will be understood to include obvious alternatives or variants.

TABLE 1

| Active Excitation | Normalisation for Absolute Response Coil Set | | | |
|---|---|---|---|---|
| $(10_n)$ | (41) | (42) | (43) | (44) |
| 1 | 1 | 0 | 0 | 0 |
| 2 | 0 | 1 | 0 | 0 |
| 3 | 0 | 0 | 1 | 0 |
| 4 | 0 | 0 | 0 | 1 |
| 5 | −1 | 0 | 0 | 0 |
| 6 | 0 | −1 | 0 | 0 |
| 7 | 0 | 0 | −1 | 0 |
| 8 | 0 | 0 | 0 | −1 |
| 9 | 1 | 0 | 0 | 0 |
| 10 | 0 | 1 | 0 | 0 |
| 11 | 0 | 0 | 1 | 0 |
| 12 | 0 | 0 | 0 | 1 |
| 13 | −1 | 0 | 0 | 0 |
| 14 | 0 | −1 | 0 | 0 |
| 15 | 0 | 0 | −1 | 0 |
| 16 | 0 | 0 | 0 | −1 |

TABLE 2

| Active Excitation | Normalisation for CP Response Coil Set | | | |
|---|---|---|---|---|
| $(10_n)$ | (41) | (42) | (43) | (44) |
| 1 | 0 | 0 | 1 | 0 |
| 2 | 0 | 0 | 0 | 1 |
| 3 | −1 | 0 | 0 | 0 |
| 4 | 0 | −1 | 0 | 0 |
| 5 | 0 | 0 | −1 | 0 |
| 6 | 0 | 0 | 0 | −1 |
| 7 | 1 | 0 | 0 | 0 |
| 8 | 0 | 1 | 0 | 0 |
| 9 | 0 | 0 | 1 | 0 |

TABLE 2-continued

| Active Excitation | Normalisation for CP Response Coil Set | | | |
|---|---|---|---|---|
| $(10_n)$ | (41) | (42) | (43) | (44) |
| 10 | 0 | 0 | 0 | 1 |
| 11 | −1 | 0 | 0 | 0 |
| 12 | 0 | −1 | 0 | 0 |
| 13 | 0 | 0 | −1 | 0 |
| 14 | 0 | 0 | 0 | −1 |
| 15 | 1 | 0 | 0 | 0 |
| 16 | 0 | 1 | 0 | 0 |

We claim:

1. A probe for measuring the depth of a defect adjacent to a material surface, comprising:

a magnetic field generator configured to generate an alternating magnetic field having two opposed pole portions of magnetic flux which interact with the material surface in first and second regions spaced apart along a spatial direction in the surface when the probe is positioned against the surface, so as to induce an eddy current flow in the surface between said two regions running across said spatial direction, said eddy current flow exhibiting a current gradient along said spatial direction, so that the defect extending in said spatial direction will give rise to a defect-crossing potential difference across the defect, said defect-crossing potential difference varying along said spatial direction as a potential difference gradient, to give rise to perturbation currents in said eddy currents; and at least one perturbation current sensor configured to sense a magnetic field normal to the surface corresponding to said perturbation currents in the plane of the surface, positioned asymmetrically relative to said magnetic field generator in the region of said potential difference gradient to provide at least one output signal dependent upon said perturbation currents and hence upon said potential difference gradient, as a quantitative measure of the depth of the defect.

2. The probe according to claim 1, wherein said magnetic field generator is arranged to generate a field having symmetrical field gradient regions about a center along said spatial direction, inducing corresponding symmetrical contra-rotating eddy current regions in the surface along said spatial direction.

3. The probe according to claim 2, wherein said at least one sensor is arranged asymmetrically with regard to said magnetic field produced by said magnetic field generator.

4. The probe according to claim 3, wherein said at least one sensor is disposed substantially to overlie regions of maximum current density gradient in the surface.

5. The probe according to claim 3, wherein said at least one sensor is positioned asymmetrically, relative to said center, in said spatial direction.

6. The probe according to claim 3, wherein said at least one sensor comprises at least one pair of perturbation current sensors positioned centrosymmetrically in said spatial direction.

7. The probe according to claim 6, wherein said at least one pair of said perturbation current sensors are connected in opposition such that induced signals of opposite sign in said sensors are additive in magnitude.

8. The probe according to claim 1, wherein said at least one sensor comprises at least one pair of perturbation current sensors offset in said spatial direction.

9. The probe according claim 1, wherein said at least one sensor comprises a coil in a plane parallel to the surface.

10. The probe according to claim 3, wherein said at least one sensor comprises a coil parallel to the surface, comprising a first lobe and second lobe, aligned in said spatial direction, said first and second lobes inducing opposing current rotations, wherein said opposing current rotations induced in said lobes are additive.

11. The probe according claim 1, wherein said magnetic field generator comprises a solenoid extending in said spatial direction.

12. A measuring assembly comprising a probe according to claim 8 and further comprising signal processing means for combining said signals from said at least one pair of said perturbation current sensors such that induced signals of opposite signs in said sensors are additive in magnitude.

13. The probe according to claim 1, wherein said magnetic field generator and said at least one sensor are packaged for use under water.

14. The probe according to claim 1, wherein said magnetic field sensed by said at least one sensor is orthogonal to said magnetic field generated by said magnetic field generator.

15. The probe according to claim 14, wherein said magnetic field generator and said at least one current sensor each consist of at least one inductance coil, and further wherein an axis of at least one of said plurality of said inductance coils of said at least one current sensor is orthogonal to an axis of said magnetic field generator.

16. The probe according to claim 1, wherein said at least one perturbation current sensor comprises an array of perturbation current sensors.

17. The probe according to claim 1, wherein the probe is shaped to conform to a non-tubular surface.

18. The probe according to claim 1, wherein said magnetic field generator includes a high frequency alternating electric excitation field equal to or greater than approximately one kHz.

19. The probe according to claim 1, wherein said magnetic field generator includes a high frequency alternating electric excitation field equal to or greater than approximately 40 kHz.

20. A method of measuring a depth of a defect in a surface of a material from a position adjacent to the material, comprising the steps of:

generating an AC eddy current in a plane of the surface, said eddy current having a region flowing across a spatial direction in which the defect extends to create a defect-crossing potential difference across the sides of the defect, said defect crossing potential difference varying along the defect in said spatial direction in a gradient along the defect, whereby perturbation currents are generated in the surface;

sensing said perturbation currents at a point in said gradient to provide sensed signals which are responsive to a magnitude of said defect-crossing potential difference; and deriving from said sensed signals a quantitative indication of the depth of said defect at a point between the ends of said defect.

21. The method according to claim 20, wherein said AC eddy current is induced by a generated magnetic field.

22. The method according to claim 20, wherein said AC eddy current is, in the absence of a defect, centrosymmetrical along said spatial direction and said sensed current perturbations are sensed or processed asymmetrically.

23. The method according to claim 20, wherein said deriving step comprises the step of processing said sensed signals to derive real and imaginary components of said perturbation currents.

24. The method according to claim 20, wherein said surface is a non-tubular surface.

25. The method according to claim 24, wherein said surface comprises a weld between two plates.

26. The method according to claim 20, wherein said generating step includes the step of generating a high frequency alternating electric excitation field equal to or greater than approximately one kHz.

27. The method according to claim 20, wherein said generating step includes the step of generating a high frequency alternating electric excitation field equal to or greater than approximately 40 kHz.

* * * * *